US010544179B2

(12) United States Patent
Geisser et al.

(10) Patent No.: US 10,544,179 B2
(45) Date of Patent: Jan. 28, 2020

(54) ORGANIC COMPOUNDS

(71) Applicant: GIVAUDAN SA, Vernier (CH)

(72) Inventors: Roger Wilhelm Geisser, Zürich (CH); Jürg Daniel Oetiker, Männedorf (CH); Fridtjof Schröder, Hettlingen (CH)

(73) Assignee: GIVAUDAN S.A., Vernier (CH)

( * ) Notice: Subject to any disclaimer, the term of this patent is extended or adjusted under 35 U.S.C. 154(b) by 0 days.

(21) Appl. No.: 15/726,970

(22) Filed: Oct. 6, 2017

(65) Prior Publication Data

US 2018/0066003 A1 Mar. 8, 2018

Related U.S. Application Data

(62) Division of application No. 15/103,556, filed as application No. PCT/EP2015/051219 on Jan. 22, 2015.

(30) Foreign Application Priority Data

Jan. 24, 2014 (GB) .................................. 1401230.6

(51) Int. Cl.
| | | |
|---|---|---|
| *B01J 23/00* | (2006.01) |
| *C07F 15/00* | (2006.01) |
| *C07B 41/02* | (2006.01) |
| *C07C 29/149* | (2006.01) |
| *C07C 29/17* | (2006.01) |
| *C07C 67/303* | (2006.01) |
| *C07D 307/79* | (2006.01) |
| *C07C 33/025* | (2006.01) |
| *C07C 33/20* | (2006.01) |
| *C07C 35/36* | (2006.01) |
| *C07C 69/612* | (2006.01) |

(52) U.S. Cl.
CPC .......... *C07F 15/0053* (2013.01); *C07B 41/02* (2013.01); *C07C 29/149* (2013.01); *C07C 29/177* (2013.01); *C07C 33/025* (2013.01); *C07C 33/20* (2013.01); *C07C 35/36* (2013.01); *C07C 67/303* (2013.01); *C07C 69/612* (2013.01); *C07D 307/79* (2013.01); *C07C 2602/28* (2017.05)

(58) Field of Classification Search
CPC ... C07F 15/0053; C07C 33/025; C07C 33/20; C07C 35/36; C07C 69/612; C07C 67/303; C07C 29/177; C07C 29/149; C07C 2602/28; C07D 307/79; C07B 41/02
USPC ............................................... 549/3; 502/325
See application file for complete search history.

(56) References Cited

FOREIGN PATENT DOCUMENTS

| WO | 9952915 A1 | 10/1999 |
| WO | 2012048646 A1 | 4/2012 |
| WO | 2013023307 A1 | 2/2013 |

OTHER PUBLICATIONS

International Search Report and Written Opinion for corresponding application PCT/EP2015/051219 dated Mar. 27, 2015.

(Continued)

*Primary Examiner* — Taylor V Oh
(74) *Attorney, Agent, or Firm* — Norris McLaughlin, PA

(57) ABSTRACT

A process for the hydrogenation of a substrate comprising a carbon heteroatom double bond in the presence of a transition metal complex comprising a tridentate or bisdentate-ligand containing a nitrogen, sulphur and phosphorus atom, of which at least the N- and P- and optionally also the S-atom coordinates with the transition metal.

8 Claims, No Drawings

(56) References Cited

OTHER PUBLICATIONS

GB Search Report for corresponding application GB 1401230.6 dated Aug. 19, 2014.

J. Schroer, et al., "Rhenium(V) complexes with tridentate, ligands", Polyhedron, Pergamon Press, Oxford, GB, vol. 33, No. 1, Nov. 16, 2011, pp. 218-222.

S. R. Bayly, et al., "Ruthenium complexes with tridentate PNX (X=O, S) donor ligands", Dalton Transactions, No. 16, Jan. 1, 2008, p. 2190.

F. Colobert, et al., "Axial Chirality Control During Suzuki-Miyaura Cross-Coupling Reactions: The tert-Butylsulfinyl Group as an Efficient Chiral Auxiliary", Organic Letters, Col. 11, No. 22, Nov. 19, 2009, pp. 5130-5133.

M. M. Mogorosi, et al., "Neutral palladium(II) complexes with, Schiff-base ligands: Synthesis, characterization and catalytic oligomerisation of ethylene", Journal of Organometallic Chemistry, Elsevier-Sequoia S.A. Lausanne, CH, vol. 696, No. 23, Jul. 29, 2011, pp. 3585-3592.

D. Wang, et al., "Yhiophene-NPN Ligand Supported Rare-Earth Metal Bis(alkyl) Complexes, Synthesis and Catalysis toward highly trans-1,4 Selective Polymerization of Butadiene", Organometallics, vol. 27, No. 24, Dec. 22, 2008, pp. 6531-6538.

M. E. Bluhm, et al., "Chromium imine and amine complexes as homogeneous catalysts for the trimerisation and polymerisation of ethylene", Journal of Organometallic Chemistry, Elsevier-Sequoia S.A. Lausanne, CH, vol. 690, No. 3, Jan. 28, 2005, pp. 713-721.

H. Li-Peng, et al., "Ethylene polymerization by the new chromium catalysts based on amino-pyrrolide ligands", Journal of Polymer Science Part A: Polymer Chemistry, vol. 47, No. 3, Feb. 1, 2009, pp. 713-721.

J. D. G. Correia, et al., "Synthesis and characterization of mixed-ligand oxorhenium(V) complexes with new [(PNO/S)(S)] donor atom sets", Journal of the Chemical Society, Dalton Transactions, No. 15, Jan. 1, 2001, pp. 2245-2250.

XP002737118, Database CA [Online] Chemical Abstracts Service, Columbus, Ohio, 1996, retrieved from STN Database accession No. 124:317485.

H. Ankersmit, et al., "Methyl-, acetyl-and allyl-palladium and platinum complexes containing novel terdentate PNS and NN's ligands", Mar. 5, 1996.

T. Morimoto, et al., "Enantioselective copper-catalyzed conjugate addition of diethylzinc to enones using new chiral P,N ligands composed of (S)-2-alkyl-2-aminoethylphosphines and alpha-substituted pyridines", Tetrahedron Letters, Pergamon, GB, vol. 41, No. 51, Dec. 16, 2000, pp. 10025-10029.

ORGANIC COMPOUNDS

The present invention relates to the field of catalytic hydrogenation of a substrate containing a carbon heteroatom double bond, using molecular hydrogen and employing a catalytic system comprising a base and a group VIII metal complex with a tri-dentate or bisdentate ligand containing a phosphorus, a nitrogen, and a sulphur coordination site. The invention also relates to said ligands and group VIII metal complexes containing said ligands.

Synthetic procedures and reagents for reducing substrates, containing functionality including esters, lactones and other carbonyl groups, into alcohols are known in the art. WO2006106483 discloses a class of bidentate ruthenium (II) complexes that is useful in the catalytic hydrogenation of these substrates and WO 2013023307 discloses a class of tridentate complexes for this purpose. Similarly, WO2006106484 discloses a class of tetradentate ruthenium complexes that are useful for this purpose.

Despite reagents and processes being known in the art for reducing substrates with functional groups containing carbon heteroatom double bonds, there remains a need for industrially acceptable reagents and processes for producing alcohols from substrates containing carbonyl groups. Especially suited for this purpose are catalysts under hydrogen pressure or hydrogen transfer conditions, which enable processes to proceed with low catalyst loading, high conversion and with high chemoselectivity for groups containing a carbon hetero-atom double bond.

The invention provides in a first aspect a process for the hydrogenation of a functional group containing a carbon heteroatom double bond, in the presence of a transition metal complex according to the general formula

MX$_2$[SNP]Y wherein M is a group VIII transition metal, for example Ru or Os, and SNP represents a tridentate or bisdentate ligand containing a nitrogen, sulphur and phosphorus atom, of which at least the N- and P- and optionally also the S-atom coordinates with the transition metal, each X is independently selected from a halide, e.g. F, Cl or Br; hydroxyl, alkoxy, acyloxy, amido, and each Y is independently selected from a monodentate phosphine or a carbon monoxide (CO) ligand, a nitrosyl group or a RCN group (R=alkyl, aryl).

When X=alkoxy, acyloxy or amido and Y=phosphine or RCN, these ligands can be optionally substituted.

The term "phosphine" includes monodentate phosphines, which are part of polyphosphines, which are linked to the metal cores M in oligomeric arrays.

In a particular embodiment of the present invention, the nitrogen atom on the tridentate or bisdentate ligand forms part of an amine group or an imine group; whereas the sulphur atom forms part of an aliphatic group or forms part of an aromatic ring; and the phosphorus atom forms part of a phosphine group.

In a particular embodiment, when the sulphur atom forms part of an aromatic ring, the ring is not a 5-membered heterocycle containing both S and N heteroatoms.

In a particular embodiment of the present invention, the nitrogen atom-containing group is flanked on one side by the phosphorus atom-containing group, and on the other side by the sulphur atom-containing group.

In a particular embodiment of the present invention the tridentate or bisdentate ligand L is represented by the formula

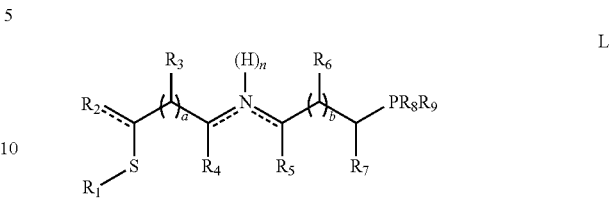

L wherein
R$_1$ and R$_2$ are independently selected from H, or C$_1$ to C$_{20}$ alkyl or aryl, which may be optionally substituted, or R$_1$ and R$_2$ are connected such that together with the sulphur and carbon atoms to which they are attached, they form a heteroaliphatic or heteroaromatic ring, which may be substituted or unsubstituted, and wherein if the ring is heteroaromatic, it is not a 5-membered heterocycle containing both S and N heteroatoms, in particular a thiazole ring;
R$_3$ through R$_7$ are independently selected from H or C$_1$ to C$_{20}$ linear or branched alkyl group or alkenyl group; C$_3$ to C$_8$ cyclic alkyl group; or a C$_5$ to C$_{10}$ aryl group, wherein any of the foregoing groups may be substituted or unsubstituted; or R$_2$ and R$_3$; R$_3$ and R$_4$; or R$_2$ and R$_4$, together with the carbon atoms to which they are attached form a 5- or 6-membered aliphatic ring, which is optionally unsaturated; and/or R$_5$ and R$_6$; R$_5$ and R$_7$; or R$_6$ and R$_7$, together with the carbon atoms to which they are attached form a 5- or 6-membered aliphatic ring, which is optionally unsaturated, wherein any of the foregoing groups may be substituted or unsubstituted; R$_8$ and R$_9$ independently are selected from H or C$_1$ to C$_{20}$ linear or branched alkyl group or alkenyl group; C$_3$ to C$_8$ cyclic alkyl group; a C$_5$ to C$_{10}$ aryl or heteroaryl group, wherein any of the foregoing groups may be substituted or unsubstituted;
a and b are independently 0, 1 or 2;
n is 0 or 1; and
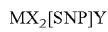 represents a single bond or a double bond, provided that when R$_2$ is H or C$_4$ to C$_{20}$ alkyl, 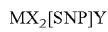 represents a single bond; and when n is 1 each N 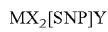 represents a carbon-nitrogen single bond; whereas when n is 0, one N 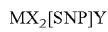 is a carbon-nitrogen single bond and the other N 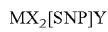 is a carbon-nitrogen double bond.

In a more particular embodiment of the present invention the tridentate or bisdentate ligands may be represented by the formula

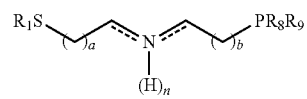

wherein
R$_1$ is H or C$_{1-20}$ alkyl, which may contain aliphatic ring systems, heteroatoms, unsaturated or aromatic groups, be substituted or unsubstituted, and are preferably methyl, ethyl, propyl, isopropyl, n-butyl, isobutyl;
R$_8$, and R$_9$ are independently as herein above defined;
a and b are independently 1 or 2;
n is 0 or 1; and
when n is 1 each N 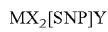 represents a carbon-nitrogen single bond; whereas when n is 0, one N 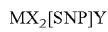 is a carbon-nitrogen single bond and the other N ===== is a carbon-nitrogen double bond.

In another particular embodiment the tridentate or bisdentate ligands may be represented by the formula

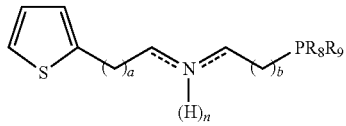

wherein $R_8$, $R_9$, a, b, n and N ===== are as defined in the immediately preceding paragraph, and the thiophene group may be unsubstituted or substituted with one or more substituents selected from $C_{1-10}$ alkyl, aryl, heteroaryl, alkenyl, nitrile, or a halide.

Particular tridentate or bisdentate ligands useful in the present invention are selected from

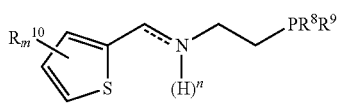

L1

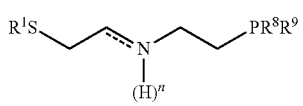

L2

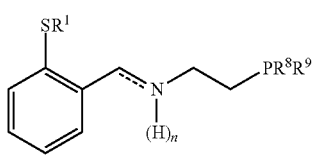

L3

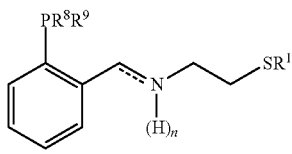

L4 wherein $R_1$ is as herein above defined, and in particular methyl, n-ethyl, n-propyl or n-butyl;

$R_8$ and $R_9$ are independently selected from $C_1$ to $C_{20}$ alkyl or phenyl, which are optionally substituted N ===== is a carbon-nitrogen single bond when n is 1 and a carbon-nitrogen double bond when n is zero; and $R^{10}$ can be any substituent but is preferentially a group selected from $C_1$ to $C_{10}$ alkyl, aryl, heteroaryl, alkenyl, nitrile, halide, all of which may be substituted or unsubstituted; or $R^{10}$ is a divalent radical that is connected to two carbon atoms in the hetero-aromatic ring and together with these carbon atoms forms a $C_5$ to $C_7$ ring; and m is 0, 1, 2 or 3

Preferred tridentate or bisdentate ligands are those hereinabove described, wherein the S-atom does not form part of a ring system. Particularly preferred are those ligands wherein $R_1$ and $R_2$ are independently selected from H or $C_1$ to $C_{20}$ alkyl or aryl groups, which may optionally be substituted. Still more particularly, the group $R_1$ is aliphatic, for example methyl or butyl. These ligands can form catalysts, which may catalyse hydrogenation of carbon-heteroatom double bonds with particularly high efficiency.

In a particular embodiment of the invention, the ligand is not a ligand selected from

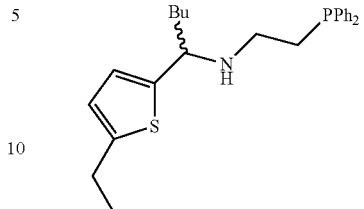

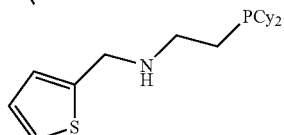

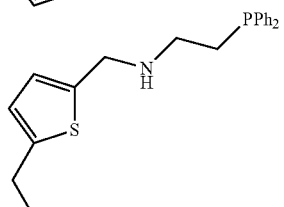

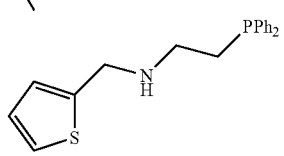

as those ligands are defined in WO 2012/048646.

In a particular embodiment of the present invention the group VIII transition metal complex has the formula $MX_2[SNP]Y$ wherein M, SNP, X, and Y are as hereinabove defined.

In a particular embodiment of the present invention the group VIII transition metal complex is selected from complexes of the formulae, wherein the S-atom is optionally coordinated to the metal atom

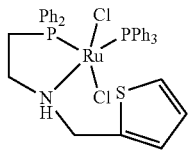

1

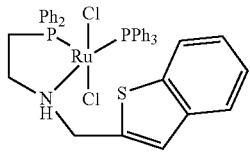

2

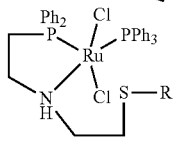

3 R = methyl
4 R = n-butyl
5 R = n-octyl

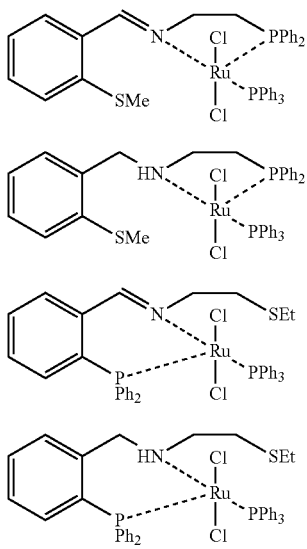

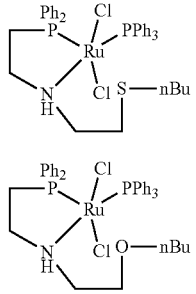

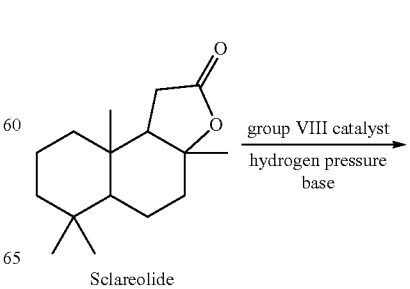

The ligands may be prepared in a straightforward manner using common starting materials and reagents, according to literature methods. The thiophene-containing SNP-ligand L1 of complex 1, for example, has been prepared in accordance with methods described in CN 102443082. The ortho-phenylene-bridged ligands L3 and L4 of complexes 6, 7 and 8 for example, have been prepared my methods similar to the ones described by M. E. Bluhm et al. in *J. Organomet. Chem.* 690, 713-721, 2005.

In contrast to the thiophene containing ligands L1, SNP ligands such as L2 with the sulphur embedded in a thioether on one side, SN- and NP-alkylidene linkages to the secondary amine NH, and the phosphorus atom embedded in a trisustituted phosphine on the other side have not been described, and represent another aspect of the invention.

Accordingly, in another aspect of the present invention there is provided the ligand according to the formula L2 described hereinabove, as well as catalysts containing said ligand.

The imines of ligands L1-L4 can be prepared, for example, by the condensation of an aldehyde with a primary amine in a suitable solvent, such as a lower alcohol, e.g. methanol. The corresponding amine can be prepared from the imine by subjecting the imine to a reducing agent, such as sodium borohydride, in a suitable solvent, such as ethanol. Both steps can be combined in a one-pot reduction amination process under conditions known to the person skilled in the art.

Once the ligands are prepared, the metal complexes of the ligands can be prepared in a manner known per se. In a general way, metal complexes of the ligands can be prepared by literature methods. For example, the ligands may simply be reacted with a suitable metal precursor, such as $RuCl_2(PPh_3)_3$ under reflux conditions in a suitable solvent, such as toluene. Alternative metal precursors such as $RuCl_2(DMSO)_4$, $RuHCl(PPh_3)_3$ can be used as well as alternative solvents such as tetrahydrofurane or dichloromethane.

The SNP ligands described herein can form either octahedral or trigonal bipyramidal transition metal complexes. This means that $RuX_2Y$ is complexed with one SNP-ligand, either via bisdentate PN-coordination or via tridentate SNP-coordination. Coordination of the weakly donating thio- or thiophene-unit at the ruthenium core is therefore optional and may change from complex to complex as well as in the course of the hydrogenation reaction, e.g. when the halides of $RuX_2$ are exchanged by hydrides. The essential feature of the $MX_2[SNP]Y$ complexes is that only one SNP-ligand is present in $MX_2[SNP]Y$ as shown by NMR, MS and elemental analysis. Thus, tridentate octahedral and bisdentate trigonal $MX_2[SNP]Y$ complexes both represent aspects of the present invention, and although the coordination of the thio- or thiophene-unit to the metal core may be optional, its presence in the SNP-ligand nevertheless improves the catalyst efficiency as demonstrated for example by comparison of the Ru(II)SNP and the Ru(II)ONP complexes 4 and 10 in the hydrogenation of Sclareolide. Thus, whereas Sclareolide underwent complete hydrogenation to Sclareodiol in the presence of 25 ppm of 4, its ONP-analogue 10 gave only 30% (conversion) of Sclareolide to Sclareodiol at 0.1% and no conversion at 0.01% level.

The metal complexes may be prepared in situ in the hydrogenation medium, without isolation or purification, shortly before their use. One suitable method for producing the metal complexes in situ is heating a 1:1 mixture of metal precursor $RuCl_2(PPh_3)_3$ and ligand in toluene at reflux for several hours, then substrate and base is added and the whole mixture is hydrogenated in an autoclave under hydrogen pressure.

The transition metal complexes described herein are useful for catalysing the hydrogenation of functionality containing a carbon-heteroatom double bond. Such functionality includes, but are not limited to esters, lactones, ketones, aldehydes, amides, lactams and imines, although they are particularly suitable for use in the hydrogenation of esters and lactones. Particularly useful substrates, bearing the aforementioned functionality containing a carbon-heteroatom double bond, are those materials that are useful in the fragrance or flavour industries, as either final products or intermediates of final products.

In a particular embodiment of the present invention Sclareolide can be hydrogenated with a transition metal complex of the present invention to an intermediate diol (Sclareodiol) and then cyclised using literature methods to the valuable fragrance ingredient Ambrox.

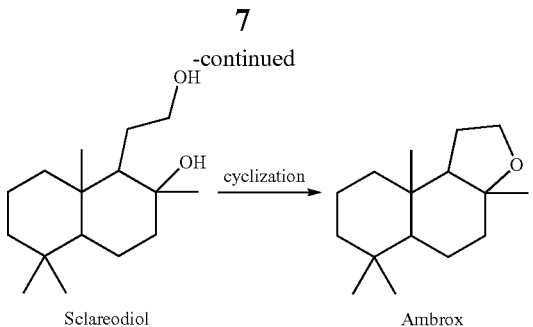

Sclareodiol → Ambrox (cyclization)

The reaction may be carried out using catalytic amounts of a transition metal complex according to the invention in the presence of a suitable base, such as potassium methoxide and under about 50 bar of hydrogen at elevated temperature, e.g. 100° C. for about 4 hours. The reaction may be carried out in a solvent, such as THF. Cyclisation may be carried out by various methods known to the person skilled in the art, as described for example in WO 2009010791.

In another aspect the catalysts of the present invention can be used to hydrogenate $C_8$-$C_{40}$ alkanoates, alkenoates and benzoates, which may be substituted or unsubstituted, to the corresponding primary alcohols. This includes the hydrogenation of mono-, di- and triesters. The substrates can be methyl esters, but more preferable ethyl- or higher esters, for example n-propyl, iso-propyl, n-butyl, tert-butyl, iso-butyl or even higher branched and unbranched esters, which may be substituted or unsubstituted.

Thus, a variety of esters can be hydrogenated with good efficiency, such as α,β-unsaturated ester 11 and unsaturated ester 13 giving alcohols 12 and unsaturated alcohol 14 respectively, in the latter case with high CO/alkene selectivity.

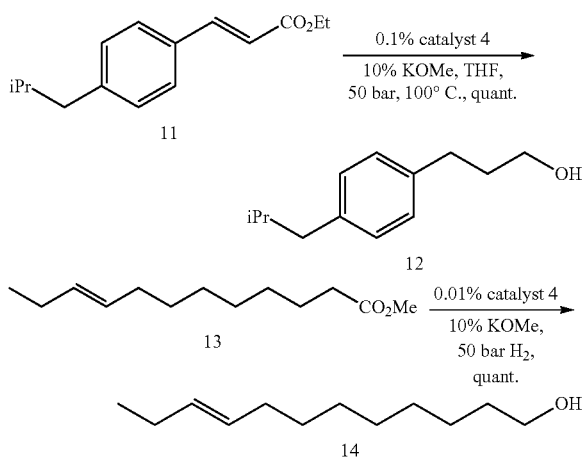

In yet another aspect the catalysts of the present invention can be used for hydrogen transfer reaction of ketones and imines to yield secondary alcohols and amines. In hydrogen transfer reactions the carbonyl group is hydrogenated by hydrogen transfer from the alcohol solvent to the carbonyl group in the presence of a base. No additional hydrogen pressure is required but can be optionally applied.

In yet another aspect the catalysts of the present invention can be used for dehydrogenation reactions. This class of reactions is the inverse of all above transformations, thus giving for example esters from alcohols under concomitant generation of hydrogen.

In the catalytic hydrogenation reaction of the present invention, the transition metal complex may be employed in amounts of 0.05 to 0.001 mol % relative to the amount of substrate.

Low catalyst levels are preferred because this can efficiently reduce the overall costs of catalytic homogeneous hydrogenation reactions.

As a base employed in the catalytic hydrogenation reaction, one can mention metal alkanoates. The metals may be Na, K or Cs; whereas the alkanoates may be $C_1$ to $C_{10}$ alkanoates, which may be linear or branched.

The metal alkanolate may be used in any amounts between 1 mol-equivalent per substrate and and 1 mol-equivalent per catalyst, but typically in amounts of 1-15% per substrate to obtain good results and to keep the cost contribution of the base low.

Another efficient group of bases consists of metal hydrides such as NaH or KH, which may be used in any amounts between 1 mol-equivalent per substrate and and 1 mol-equivalent per catalyst, but typically in amounts of 1-15% per substrate to obtain good results and to keep the cost contribution of the base low. These bases are typically provided as dispersions in mineral oil, the bases can be either used in this form in the hydrogenation reaction or the oils can be washed out prior to hydrogenation.

The solvent employed in the base/solvent system can be any solvent that is typically employed in homogeneous catalytic hydrogenation reactions. Non-limiting examples of solvents include aromatic solvents such as toluene or xylenes; hydrocarbon solvents such as hexane or cyclohexane; ethers such as tetrahydrofuran or MTBE; and polar solvents such as tert-butanol. Methanol should be avoided. Preferred solvents are ethers or furanes such as THF or analogues such as cyclopentyl methyl ether (CPME), methyltetrahydrofurane, but any acyclic or cyclic polyethers such as dioxane or tetraethyleneglykoldiethyl ether can be also used.

Low levels of solvent, or even solvent-free systems may be employed. Low levels of solvent include <100% solvent per substrate in weight equivalents (w/w), <50% w/w, <25% w/w or preferable <10% w/w.

When a solvent is employed, its use can be limited to an amount just sufficient for catalyst dissolution/emulsification and for subsequent transfer and addition of the thus-prepared catalyst solution to the substrate. However, the catalyst can be also added in solid form. Apart from these negligible solvent-quantities the reaction can be carried out essentially solvent-free.

Under strict solvent-free conditions the catalyst is dissolved in a fraction of the substrate before this fraction is added to the remaining substrate or vice versa. The catalyst can be nevertheless also added in solid form.

Particularly efficient base/solvent systems include KOMe in THF, NaOMe in toluene, KotBu in tBuOH, NaH in THF or KH in toluene.

The catalytic hydrogenation reaction may be carried out in an autoclave at a $H_2$ pressure ranging from 1 to 80 bars, or even higher, more particularly 40 to 80 bar or higher. The skilled person will understand that the $H_2$ pressure may be adjusted to optimise for the level of transition metal complex used.

The temperature at which the reaction may be carried out may vary depending on such factors as the melting/boiling point, the viscosity and the polarity of the substrate employed and the reaction products as well as the desired reaction time to achieve full, or substantially full conversion.

Typically, however, the reaction will be carried out between 50 and 120 degrees centigrade.

There now follows a series of examples that further act to illustrate the invention.

GENERAL ANALYTICAL CONDITIONS

Non-polar GCMS: 50° C./2 min, 20° C./min 200° C., 35° C./min 270° C. GC/MS Agilent 5975C MSD with HP 7890A Series GC system. Non-polar column: BPX5 from SGE, 5% phenyl 95% dimethylpolysiloxan 0.22 mm×0.25 mm×12 m. Carrier Gas: Helium. Injector temperature: 230° C. Split 1:50. Flow: 1.0 ml/min. Transfer line: 250° C. MS-quadrupol: 106° C. MS-source: 230° C.

EXAMPLE 1: RuCl$_2$(2-(diphenylphosphino)-N-(thiophen-2-ylmethyl)ethanamine)PPh$_3$ 1

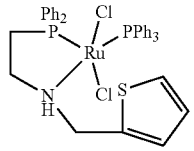

Under nitrogen and stirring NaBH(OAc)$_3$ (4.4 g, 20 mmol) is added to 2-(diphenylphosphino)-ethanamine (3 g, 12.4 mmol) and thiophene-2-carbaldehyde (1.6 g, 13.7 mmol) in 1,2-dichloroethane (75 ml). After 18 h stirring at room temperature the mixture is poured upon conc. NaHCO$_3$ (100 ml) and extracted with ethyl acetate. The organic layers are washed with water and conc. aqueous NaCl. The aqueous phase is re-extracted with ethyl acetate. The combined organic layers are dried over MgSO$_4$, filtered and evaporated to give 4.6 g of a yellow oil which is taken up in t-butyl methyl ether and purified by flash chromatography over silica gel using eluent t-butyl methyl ether. The first fraction (1.85 g) contains the double alkylation product (tertiary amine) and is discarded, the second fraction (1.1 g, 27%) contains SNP-ligand 2-(diphenylphosphino)-N-(thiophen-2-ylmethyl)-ethanamine as yellowish oil. Analytical data:

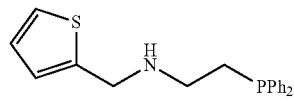

$^1$H-NMR (CD$_2$Cl$_2$, 400 MHz): δ 7.38-7.43 (4 H, Ar), 7.28-7.31 (6 H, Ar), 7.2 (m, 1 H, Thiophen-CH), 6.9 (m, 1 H, Thiophen-CH), 6.85 (m, 1 H, Thiophen-CH), 3.9 (d, J=1.01 Hz, 2 H, CH$_2$N), 2.69-2.84 (m, 2 H, NCH$_2$CH$_2$P), 2.20-2.30 (m, 2 H, NCH$_2$CH$_2$P), 1.7 (s, 1 H, NH) ppm. $^{13}$C-NMR (CD$_2$Cl$_2$, 400 MHz): δ 144.6 (s), 138.8 and 138.7 (s), 132.7 and 132.6 (s), 128.6 and 128.5 (d), 128.4 (d), 126.5 (d), 124.6 (d), 124.15 (d), 48.05 (t), 45.9 and 45.7 (t), 28.9 and 28.8 (t) ppm. $^{31}$P-NMR (CD$_2$Cl$_2$, 200 MHz): −21.5 ppm. MS (EI) (%) (m/z): 325 ([M]$^+$, 17%), 292 ([M−HS]$^+$, 20%), 268 ([M−C$_2$HS]$^+$, 15%), 186 ([HPPh$_2$]$^+$, 100%), 97 ([CH$_2$-thiophen]$^+$, 50%).

SNP-ligand 2-(diphenylphosphino)-N-(thiophen-2-ylmethyl)ethanamine (0.16 g, 0.5 mmol) and RuCl$_2$(PPh$_3$) 3 (0.5 g, 0.5 mmol) in dichloromethane (15 ml) are heated under reflux, stirring and nitrogen for 24 h. At room temperature hexane (60 ml) are added. The precipitate is filtered, washed with hexane (3×20 ml) and dried under reduced pressure to give complex 1 (0.21 g, 55%) as a brick red powder. Analytical data of 1:

$^1$H-NMR (CD$_2$Cl$_2$, 400 MHz): δ 2.3-2.43 (m, 1 H), 2.76-2.87 (m, 1 H), 3.3-3.5 (m, 2 H), 4.07-4.15 (m, 1 H), 4.39-4.46 (m, 1 H), 4.56-4.68 (m, 1 H), 6.00 (d, J=5.3 Hz, 1 H), 6.85-7.58 (m, 30 H) ppm. $^{31}$P-NMR (CD$_2$Cl$_2$, 200 MHz): δ 42.79 (d, $^2$J$_{P,P}$=34 Hz, 1 P), 60.0 (d, $^2$J$_{P,P}$=33 Hz, 1 P). MS (EI) (%) (m/z): 480 ([M−Cl+Na]$^+$, 748%). Anal. calcd. for C$_{37}$H$_{35}$Cl$_2$NP$_2$RuS: C, 58.50%; H, 4.64%; N, 1.84%. Found: C, 58.42%; H, 4.92%; N, 1.74%.

EXAMPLE 2: RuCl$_2$(2-(diphenylphosphino)-N-(thiophen-2-ylmethyl)ethanamine)PPh$_3$ 2

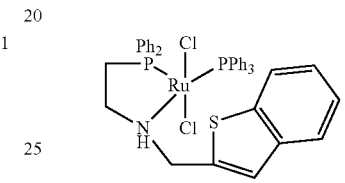

Under nitrogen and stirring NaBH(OAc)$_3$ (1.5 g, 6.6 mmol) is added to 2-(diphenylphosphino)ethanamine (1 g, 4.1 mmol) and thiophene-2-carbaldehyde (0.7 g, 4.1 mmol) in 1,2-dichloroethane (25 ml). After 19 h stirring at room temperature the mixture is poured upon conc. NaHCO$_3$ and extracted with ethyl acetate. The organic layers are washed with water and conc. aqueous NaCl. The aqueous phase is re-extracted with ethyl acetate. The combined organic layers are dried over MgSO$_4$, filtered and evaporated to give 1.7 g of a yellow oil which is taken up in ethyl acetate and purified by flash chromatography over silica gel using eluent ethyl acetate. Evaporation of the solvent gives SNP-ligand N-(benzo[b]thiophen-2-ylmethyl)-2-(diphenyl-phosphino)ethanamine (0.32 g, 21%). Analytical data:

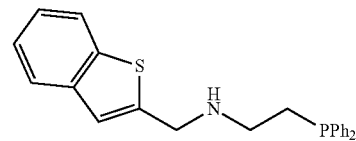

$^1$H-NMR (CDCl$_3$, 400 MHz): δ 7.79 (d, 1 H), 7.68 (d, 1 H), 7.4-7.45 (4 H), 7.25-7.35 (8 H), 7.05 (s, 1 H), 4.0 (d, 2 H, CH$_2$N), 2.85 (m, 2 H, NCH$_2$CH$_2$), 2.3 (m, 2 H, NCH$_2$CH$_2$), 1.72 (br. s., 1 H, NH) ppm. $^{13}$C-NMR (CDCl$_3$, 400 MHz): δ 145.1 (s), 139.8 (s), 139.7 (s), 138.4 and 138.3 (2 s), 132.8 and 132.65 (d), 128.7 and 128.5 (d), 128.4 (d), 129.01 (s, 1 C), 124.1 (d), 123.8 (d), 123.1 (d), 122.4 (d), 121.2 (d), 48.8 (t), 45.85 and 45.65 (t), 29.1 and 28.95 (t) ppm. $^{31}$P-NMR (CDCl$_3$, 400 MHz): −20.9 ppm. MS (EI) (%) (m/z): 375 ([M]$^+$, 23%), 324 (7%), 318 (18%), 266 (22%), 200 (15%), 199 (17%), 186 ([HPPh$_2$]$^+$, 100), 185 (10%), 183 (17%), 162 (15%), 152 (14%), 147 (48%), 121 (13%), 108 (30%).

SNP-Ligand N-(benzo[b]thiophen-2-ylmethyl)-2-(diphenylphosphino)ethanamine (0.17 g, 0.45 mmol) and RuCl$_2$(PPh$_3$) 3 (0.45 g, 0.45 mmol) in dichloromethane (13 ml) are heated under reflux, stirring and nitrogen for 24 h. At room temperature hexane (60 ml) are added ed. The precipitate is filtered, washed with hexane and dried under reduced pressure to give complex 2 (0.32 g, 88%) as a pink powder. Analytical data:

$^1$H-NMR (CD$_2$Cl$_2$, 400 MHz): δ 6.9-7.8 (30 H), 5.85 (d), 4.8 (m), 4.6 (t), 4.2 (m), 3.3-3.7, 2.85 (m), 2.35 (m), 1.6 (1 H), with 6 H from 2.35 to 5.85 ppm. $^{31}$P-NMR (CD$_2$Cl$_2$, 400 MHz): δ 57.2 (d), 43.1 (d). MS (EI in MeOH, HCO$_2$H, %, m/z): 784 ([M−Cl−HCl+HCO$_2$H]$^+$, 100%), 738 ([M−Cl−HCl]$^+$, 15%). Anal. calcd. for C$_{41}$H$_{37}$Cl$_2$NP$_2$RuS: C, 60.82%; H, 4.61%; N, 1.73%. Found: C, 60.25%; H, 4.53%; N, 1.56%.

EXAMPLE 3: RuCl$_2$(2-(diphenylphosphino)-N-(2-(methylthio)ethyl)ethanamine)PPh$_3$ 3

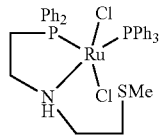

3

Methylthioethanal was prepared as described in Synthesis 7, 659 (1987) from (2,2-dimethoxyethyl)(methyl)sulfane.

Under nitrogen and stirring NaBH(OAc)$_3$ (3 g, 13.3 mmol) is added to 2-(diphenylphosphino)-ethanamine (2 g, 8.3 mmol) and methylthioethanal (0.85 g, 9.1 mmol) in 1,2-dichloroethane (50 ml). After 18 h stirring at room temperature the mixture is poured upon conc. NaHCO$_3$ and extracted with ethyl acetate. The organic layers are washed with water and conc. aqueous NaCl. The aqueous combined aqueous layers are re-extracted with ethyl acetate. The combined organic layers are dried over MgSO$_4$, filtered and evaporated to give 2.83 g of a yellowish oil which is taken up in ethyl acetate and purified by flash chromatography over silica gel using eluent ethyl acetate. Evaporation of the solvent gives SNP-ligand 2-(diphenylphosphino)-N-(2-(methylthio)ethyl)ethanamine (0.79 g, 31%). Analytical data:

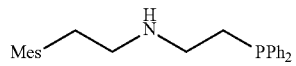

$^1$H-NMR (CD$_2$Cl$_2$, 400 MHz): δ 7.4-7.45 (4 H, Ar), 7.3-7.35 (6 H, Ar), 2.7-2.8 (4 H), 2.5-2.6 (m, 2 H), 2.2-2.3 (m, 2 H), 2.05 (3 H), 1.7 (br, 1 H, NH) ppm. $^{13}$C-NMR (CD$_2$Cl$_2$, 400 MHz): δ 138.8 (s), 132.7 (d), 128.4-128.8 (2 d), 47.8 (t), 46.3 and 46.1 (t), 34.4 (t), 29.1 and 28.9 (t), 15.1 (q, SMe) ppm. $^{31}$P-NMR (CD$_2$Cl$_2$, 200 MHz): −20.7 ppm. GSMS (EI) (%) (m/z): 288 ([M−CH$_3$]$^+$, 8%), 256 ([M+O−MeSH]$^+$, 80%), 242 (8%), 199 (19%), 185 (100%), 183 (89%), 152 (11%), 121 (27%), 108 (20%), 107 (21%), 91 (11%), 75 (43%), 61 (14%).

SNP-Ligand 2-(diphenylphosphino)-N-(2-(methylthio)ethyl)ethanamine (0.165 g, 0.54 mmol) and RuCl$_2$(PPh$_3$)$_3$ (0.52 g, 0.54 mmol) in dichloromethane (15 ml) are heated under reflux, stirring and nitrogen for 16 h. At room temperature hexane (60 ml) are added. The precipitate is filtered, washed with hexane and dried under reduced pressure to give complex 3 (0.27 g, 86%) as a greenish powder. Analytical data:

$^{31}$P-NMR (CD$_2$Cl$_2$, 400 MHz): δ 46.1 and 44.7 (2 d, 30.5 Hz, major isomer), 46.6 and 44.4 (2 d, 32.5 Hz, minor isomer). MS (EI in MeOH, HCO$_2$H, %, m/z): 776 ([M+0+Na]$^+$, 100%), 735 and 737 ([M]$^+$, 15%), 718 ([M−Cl+O]$^+$, 35%), 702 ([M−Cl]$^+$, 55%). Anal. calcd. for C$_{35}$H$_{37}$Cl$_2$NP$_2$RuS: C, 56.99%; H, 5.06%; N, 1.9%. Found: C, 55.59%; H, 5.00%; N, 2.17%.

EXAMPLE 4: RuCl$_2$(2-(diphenylphosphino)-N-(2-(n-butylthio)ethyl)ethanamine)PPh$_3$ 4

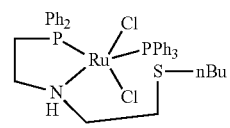

4

For the synthesis of n-butylthioethanal see N. A. Keiko et al. *Arkivoc* 127-138 (2011).

Under nitrogen and stirring NaBH(OAc)$_3$ (3 g, 13.3 mmol) is added to 2-(diphenylphosphino)-ethanamine (2 g, 8.3 mmol) and n-butylthioethanal (1.2 g, 9.1 mmol) in 1,2-dichloroethane (50 ml). After 22 h stirring at room temperature the mixture is poured upon conc. NaHCO$_3$ and is extracted with DCE. The organic layers are washed with conc. aqueous NaCl. The aqueous phase is re-extracted with DCE. The combined organic layers are dried over MgSO$_4$, filtered and evaporated to give 3.15 g of a yellowish oil which is taken up in ethyl acetate and purified by flash chromatography over silica gel using eluent ethyl acetate. In a first fraction byproduct 2-(butylthio)-N-(2-(butylthio)ethyl)-N-(2-(diphenylphosphino)ethyl)ethanamine (0.72 g, 19%, after solvent evaporation) is separated. Analytical data:

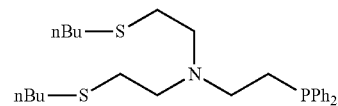

$^1$H-NMR (CD$_2$Cl$_2$, 400 MHz): δ 7.4 (4 H, Ar), 7.3 (6 H, Ar), 2.7-2.6 (6 H), 2.45-2.55 (8 H), 2.2 (2 H), 1.5-1.6 (4 H), 1.35-1.45 (4 H), 0.9 (t, 6 H) ppm. $^{13}$C-NMR (CD$_2$Cl$_2$, 400 MHz): δ 138.8 (s), 132.65 (d), 130.55 (d), 128.55 (d), 53.9 (t), 50.2 (t), 32.0 (t), 29.8 (t), 25.7 (t), 22.0 (t), 13.5 (q, Me) ppm. $^{31}$P-NMR (CD$_2$Cl$_2$, 200 MHz): −20.0 ppm. MS (EI) (m/z): 404 ([M−C4H9]$^+$), 373 (23%), 372 (90%), 358 (100%), 288 (6%), 256 (8%), 186 (9%), 185 (61%), 183 (25%), 117 (55%), 61 (16%). 57 (11%). IR (film): 3052 (w), 2954 (m), 2926 (m), 2870 (m), 1738 (w), 1586 (w), 1480 (w), 1457 (m), 1434 (m), 1377 (w), 1294 (w), 1192 (m), 1095 (m), 1069 (w), 1026 (w), 998 (w), 914 (w), 737 (m), 695 (s).

Evaporation of the solvent from the second fraction gives SNP-ligand 2-(diphenylphosphino)-N-(2-(methylthio)ethyl)ethanamine (0.72 g, 25%). Analytical data:

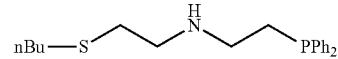

$^1$H-NMR (CD$_2$Cl$_2$, 400 MHz): δ 7.4-7.45 (4 H, Ar), 7.3-7.35 (6 H, Ar), 2.7 (4 H), 2.6 (m, 2 H), 2.5 (2 H), 2.3 (m,

2 H), 1.6 (br, 1 H, NH), 1.5 (m, 2 H), 1.4 (m, 2 H), 0.9 (t, 3 H) ppm. $^{13}$C-NMR (CD$_2$Cl$_2$, 400 MHz): δ 138.85 (s), 132.65 (d), 130.55 (d), 128.45 (d), 48.5 (t), 46.2 (t), 32.3 (t), 31.9 (t), 31.6 (t), 28.95 (t), 22.0 (t), 13.5 (q, Me) ppm. $^{31}$P-NMR (CD$_2$Cl$_2$, 200 MHz): −20.7 ppm. MS (EI) (m/z): 346 ([M+H]$^+$, 289 (10%), 288 (55%), 257 (18%), 256 ([M+O−BuSH]$^+$, 100%), 242 (20%), 199 (13%), 186 (18%), 185 (87%), 183 (31%), 69 (20%). IR (film): 3051 (w), 2926 (m), 2871 (w), 1953 (w), 1886 (w), 1812 (w), 1737 (w), 1671 (w), 1585 (w), 1479 (w), 1456 (m), 1433 (m), 1376 (w), 1331 (w), 1272 (w), 1240 (w), 1184 (w), 1117 (m), 1068 (w), 998 (w), 737 (m), 694 (s).

SNP-ligand 2-(diphenylphosphino)-N-(2-(n-butylthio) ethyl)ethanamine (0.25 g, 0.7 mmol) and RuCl$_2$(PPh$_3$)$_3$ (0.71 g, 0.7 mmol) in dichloromethane (15 ml) are heated under reflux, stirring and nitrogen for 14 h. At room temperature hexane (100 ml) are added. The precipitate is filtered, washed with hexane and dried under reduced pressure to give complex 4 (0.44 g, 78%) as an orange powder. Analytical data:

$^1$H-NMR (400 MHz, CD$_2$Cl$_2$): 6.9-7.4 (25 H), 4.5 and 4.7 (1 H), 2.3-3.7 (9 H), 1.55 (2H), 1.0-1.5 (4 H), 0.8 (t, 3H). $^{31}$P-NMR (CD$_2$Cl$_2$, 400 MHz): δ 45.6 and 45.9 (2 d), 44.7 and 44.8 (2 d). MS (ESI(+) in MeOH, HCO$_2$H, %, m/z): 754 ([M−Cl−HCl+HCO$_2$H]$^+$, 100%, identical with calculated isotope cluster), 744 ([M−Cl]$^+$, 100%). Anal. calcd. For C$_{38}$H$_{43}$Cl$_2$NP$_2$RuS: C, 58.53%; H, 5.56%; N, 1.80%. Found: C, 57.21%; H, 5.44%; N, 1.75%. IR (ATR): 3162 (w), 3059 (w), 2947 (w), 2859 (w), 1585 (w), 1480 (w), 1454 (m), 1432 (m), 1303 (w), 1267 (w), 1187 (w), 1156 (w), 1138 (w), 1088 (m), 1067 (w), 1027 (w), 1006 (w), 983 (m), 914 (w), 865 (w), 799 (w), 751 (w), 740 (m), 737 (m), 691 (s), 657 (m), 619 (m).

EXAMPLE 5: RuCl$_2$(2-(diphenylphosphino)-N-(2-(n-octylthio)ethyl)ethanamine)PPh$_3$ 5

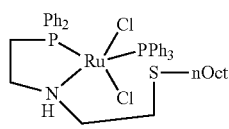

For the synthesis of n-octylthioethanal see N. A. Keiko et al. Arkivoc 127-138 (2011).

Under argon and stirring NaBH(OAc)$_3$ (2.8 g, 12.5 mmol) is added to 2-(diphenylphosphino)-ethanamine (1.9 g, 2.8 mmol) and n-octylthioethanal (1.6 g, 8.6 mmol) in 1,2-dichloroethane (50 ml). After 22 h stirring at room temperature the mixture is poured upon conc. NaHCO$_3$ and is extracted with DCE. The organic layers are washed with conc. aqueous NaCl. The aqueous phase is re-extracted with DCE. The combined organic layers are dried over MgSO$_4$, filtered and evaporated to give 3.6 g of a yellowish oil which is taken up in ethyl acetate and purified by flash chromatography over silica gel with eluent ethyl acetate to give after evaporation of the solvent 0.64 g (20%) of the ligand as colourless oil. Analytical data:

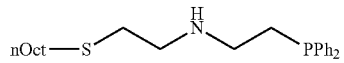

$^1$H-NMR (CD$_2$Cl$_2$, 400 MHz): δ 7.4-7.5 (4 H, Ar), 7.25-7.35 (6 H, Ar), 2.8 (4 H), 2.6 (m, 2 H), 2.5 (m, 2 H), 2.3 (m, 2 H), 1.8 (br, 1 H, NH), 1.5-1.6 (m, 2 H), 1.3-1.4 (4 H), 1.25 (6 H), 0.9 (t, 3H) ppm. $^{13}$C-NMR (CD$_2$Cl$_2$, 400 MHz): δ 138.35 (s), 132.7 (d), 128.6 (d), 128.4 (d), 48.4 (t), 46.25 (t, CH$_2$—P), 32.3 (t), 32.0 (t), 31.8 (t), 29.8 (t), 29.2 (t), 29.1 (t), 29.0 (t), 28.9 (t), 22.7 (t), 14.1 (q, Me) ppm. $^{31}$P-NMR (CD$_2$Cl$_2$, 200 MHz): −20.6 ppm. MS (EI) (m/z): 400 ([M−H]$^+$, 1%), 289 (12%), 288 (57%), 257 (19%), 256 ([M+O−OctSH]$^+$, 100%), 242 (19%), 200 (7%), 199 (8%), 186 (15%), 185 (56%), 183 (26%), 121 (7%).

SNP-ligand 2-(diphenylphosphino)-N-(2-(n-octylthio) ethyl)ethanamine (0.5 g, 1.25 mmol) and RuCl$_2$(PPh$_3$) 3 (0.86 g, 0.87 mmol) in dichloromethane (30 ml) are heated under reflux, stirring and nitrogen for 24 h. At room temperature hexane (100 ml) is slowly added under stirring. The orange precipitate is filtered, washed with hexane (3×20 ml) and dried under reduced pressure to give crude complex 5 (0.51 g, 71%) as an orange powder which is taken up again in dichoromethane (30 ml) and treated again with hexane (150 ml), slowly and under stirring. The orange precipitate is filtered, washed with hexane (3×20 ml) and dried under reduced pressure to give complex 5 (0.3 g, 29%) as an orange powder $^1$H-NMR (400 MHz, CD$_2$Cl$_2$): 6.9-7.5 (25 H), 4.55 and 4.8 (1 H), 2.3-3.6 (10 H), 1.0-1.6 (12 H), 0.9 (t, 3H). $^{31}$P-NMR (CD$_2$Cl$_2$, 400 MHz): δ 46.3, 46.1, 45.8, 45.6 and 44.7, 44.5, 44.1, 44.0. Anal. calcd. For C$_{42}$H$_{51}$Cl$_2$NP$_2$RuS: C, 60.35%; H, 6.15%; N, 1.68%. Found (after 1$^{st}$ precipitation): C, 60.00%; H, 6.31%; N, 1.52%. Found (after 2$^{nd}$ precipitation): C, 60.24%; H, 6.24%; N, 1.83%. IR (ATR): 3162 (w), 3054 (w), 2957 (w), 2921 (w), 2853 (w), 1481 (w), 1455 (w), 1432 (m), 1304 (w), 1188 (w), 1088 (m), 1072 (w), 1002 (w), 979 (m), 862 (m), 799 (w), 740 (m), 737 (m), 691 (s), 658 (m).

EXAMPLE 6: Dichloro[(N-(2-(diphenylphosphino) benzylidene)-2-(ethylthio)ethanamine) (triphenylphosphine)]-ruthenium(II) 6

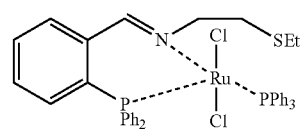

Under argon a solution of 2-(ethylthio)ethanamine (0.36 g, 3.44 mmol) in THF (3 ml) is added to a solution of 2-(diphenylphosphino)benzaldehyde (1.00 g, 3.44 mmol) in THF (10 ml). After stirring for 12 h at 72° C. the reaction mixture is cooled to 0° C., DCM (3 ml) is added and the solvents are evaporated under vacuo. SNP-ligand N-(2-(diphenylphosphino)benzylidene)-2-(ethylthio)ethan-amine is obtained as an orange solid (1.20 g, 92%). Analytical data:

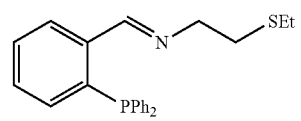

$^1$H-NMR (400 MHz, CDCl$_3$): 8.92 (d, J=4.80, 1H), 8.00 (m, 1H), 7.41 (m, 1H), 7.38-7.28 (m, 11H), 6.91 (m, 1H), 3.70 (dt, J=1.26, 7.07, 2H), 2.62 (t, J=7.33, 2H), 2.50 (q, J=7.33, 2H), 1.23 (t, J=7.33, 3H). $^{13}$C-NMR (400 MHz, CDCl$_3$): 161.12, 139.67, 137.93, 136.96, 136.87, 134.42, 133.77, 130.74, 129.28, 129.01, 128.13, 61.64, 32.56, 26.49, 15.28. $^{31}$P-NMR (500 MHz, CDCl$_3$): −13.55 (s, 1P). GC/MS: 377 (6%, M$^+$), 348 (54%, [M−29]$^+$), 288 (100%), 226 (20%), 208 (14%), 183 (28%), 165 (14%), 107 (11%), 89 (34%), 61 (14%).

Under argon dichlorotris(triphenylphosphine)ruthenium (II) (1.52 g, 1.58 mmol) is added to a solution of N-(2-(diphenylphosphino)benzylidene)-2-(ethylthio)ethanamine (0.60 g, 1.58 mmol) in toluene (13 ml). After stirring for 19 h at 110° C. the reaction mixture is cooled to room temperature and evaporated under vacuo to a volume of 5 ml. To this red suspension DCM (20 ml) is added. After stirring for 15 min the suspension is filtered and dried under vacuo. Complex 6 is obtained as a red solid (0.88 g, 69%). Analytical data:

$^1$H-NMR (400 MHz, CDCl$_3$): 8.80 (d, J=8.84, 1H), 7.56-6.81 (m, 29H), 6.35 (m, 2H), 4.60 (m, 1H), 4.20 (m, 1H), 3.03 (m, 2H), 2.29 (m, 1H), 0.92 (t, J=7.33, 3H). $^{31}$P-NMR (500 MHz, CDCl$_3$): 45.68 (d, J=30.23, 1P), 29.60 (d, J=30.23, 1P). MS (ESI): 811.10 (40%, M$^+$), 776.12 (100%, [M−Cl]$^+$). Anal. calcd. for C$_{41}$H$_{39}$Cl$_2$NP$_2$RuS: C, 60.66%; H, 4.84%; N, 1.73%. Found: C, 60.85%; H, 4.90%; N, 1.64%.

EXAMPLE 7: Dichloro[(N-(2-(diphenylphosphino)benzyl)-2-(ethylthio)ethanamine)(triphenyl-phosphine)]ruthenium(II) 7

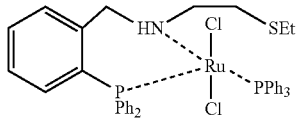

Under argon NaBH$_4$ (0.18 g, 4.75 mmol) is added to a solution of N-(2-(diphenylphosphino)-benzylidene)-2-(ethylthio)ethanamine (0.60 g, 1.58 mmol) in ethanol (6 ml). After stirring for 18 h at 78° C. the reaction mixture is cooled to room temperature and water (18 ml) is added, followed by saturated aqueous NH$_4$Cl. The phases were separated and the aqueous phase is extracted with DCM (3×10 ml). The combined organic phases are dried over MgSO$_4$, filtered and concentrated under vacuo. SNP-ligand N-(2-(diphenylphosphino)benzyl)-2-(ethylthio)ethanamine is obtained as an orange liquid (0.53 g, 88%). Analytical data:

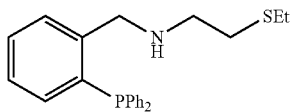

$^1$H-NMR (400 MHz, CDCl$_3$): 7.63 (m, 1H), 7.50 (m, 1H), 7.37-7.26 (m, 10H), 7.19 (dt, J=1.26, 7.58, 1H), 6.91 (m, 1H), 4.03 (d, J=1.77, 2H), 2.73 (t, J=6.82, 2H), 2.53 (t, J=6.57, 2H), 2.48 (q, J=7.33, 2H), 1.23 (t, J=7.33, 3H). $^{13}$C-NMR (400 MHz, CDCl$_3$): 137.07, 136.21, 134.36, 134.14, 132.37, 129.55, 129.43, 129.15, 128.97, 127.78. $^{31}$P-NMR (500 MHz, CDCl$_3$): −16.06 (s, 1P). MS (EI): 379.4 (2%, M$^+$), 318.3 (100%, [M−61.1]$^+$), 304.3 (15%, [M−75.1]$^+$), 275.2 (42%, [M−104.2]$^+$).

Under argon dichlorotris(triphenylphosphine)ruthenium (II) (1.22 g, 1.27 mmol) is added to a solution of N-(2-(diphenylphosphino)benzyl)-2-(ethylthio)ethanamine (0.48 g, 1.27 mmol) in toluene (17 ml). After stirring for 18 h at 110° C. the reaction mixture is cooled to room temperature and evaporated under vacuo to a volume of 5 ml. To this red suspension diethyl ether (15 ml) is added. After stirring for 15 min the suspension is filtered and dried under vacuo. Complex 7 is obtained as a red solid (0.39 g, 38%). Analytical data:

$^1$H-NMR (400 MHz, CDCl$_3$): 7.73-7.15 (m, 22H), 6.89 (m, 4H), 6.63 (m, 1H), 6.08 (m, 2H), 4.49 (m, 1H), 4.06 (m, 1H), 3.59 (m, 1H), 3.44 (m, 1H), 3.08 (m, 3H), 2.23 (m, 1H), 1.72 (m, 1H), 0.86 (t, J=7.33, 3H). $^{31}$P-NMR (500 MHz, CDCl$_3$): 35.94 (d, J=75.78, 1P), 34.74 (d, J=76.05, 1P). MS (ESI): 813.11 (34%, M$^+$), 778.14 (100%, [M−Cl]$^+$). Anal. calcd. for C$_{41}$H$_{41}$Cl$_2$NP$_2$RuS: C, 60.44%; H, 5.26%; N, 1.72%. Found: C, 60.48%; H, 4.93%; N, 1.59%.

EXAMPLE 8: Dichloro[(N-(2-(diphenylphosphino)benzyl)-2-(ethylthio)ethanamine)(triphenyl-phosphine)]ruthenium(II) 8

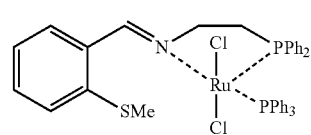

Under argon 2-(methylthio)benzaldehyde (0.33 g, 2.18 mmol) is added to a solution of 2-(di-phenylphosphino)ethanamine (0.50 g, 2.18 mmol) in methanol (6 ml). After stirring for 42 h at 75° C. the reaction mixture is cooled to room temperature and evaporated under vacuo. SNP-ligand 2-(diphenylphosphino)-N-(2-(methylthio)benzylidene)ethanamine is obtained as a light-brown solid (0.66 g, 84%). Analytical data:

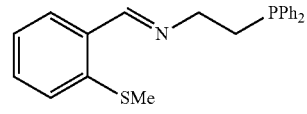

$^1$H-NMR (500 MHz, CDCl$_3$): 8.74 (s, 1H), 7.79 (dd, J=1.58, 7.88, 1H), 7.52-7.48 (m, 4H), 7.39-7.32 (m, 8H), 7.21 (m, 1H), 3.80 (m, 2H), 2.53 (m, 2H), 2.48 (s, 3H). $^{13}$C-NMR (500 MHz, CDCl$_3$): 159.37, 138.34, 134.24, 132.88, 132.74, 130.78, 130.66, 128.59, 128.49, 128.44, 128.25, 127.28, 125.50, 58.58, 29.99, 16.90. $^{31}$P-NMR (500 MHz, CDCl$_3$): −19.04 (s, 1P). GC/MS: 363 (2%, M), 348 (2%, [M−15]$^+$), 320 (100%, [M−43]$^+$), 288 (10%), 214 (12%), 183 (39%), 121 (20%), 108 (42%).

Under argon dichlorotris(triphenylphosphine)ruthenium (II) (0.53 g, 0.55 mmol) is added to a solution of 2-(diphenylphosphino)-N-(2-(methylthio)benzylidene)ethanamine (0.20 g, 0.55 mmol) in toluene (15 ml). After stirring for 20 h at 110° C. the reaction mixture is cooled to room temperature and evaporated under vacuo to a volume of 5 ml. To this red suspension hexane (20 ml) is added. After stirring for 15 min the suspension is filtered and washed with hexane (4 ml). The red filter cake is dried under vacuo for 19 h and then suspended in diethyl ether (6 ml). The suspension is filtered, washed with diethyl ether (4×4 ml) and the filter cake is dried under vacuo. Complex 8 is obtained as a light-red solid (0.29 g, 67%). Analytical data:

$^1$H-NMR (400 MHz, CDCl$_3$): 8.78 (d, J=8.84, 1H), 8.33 (m, 1H), 7.70 (m, 3H), 7.54-7.06 (m, 25H), 4.59 (m, 1H), 4.53 (m, 1H), 2.55 (m, 2H), 1.83 (d, J=2.53, 3H). $^{31}$P-NMR (500 MHz, CDCl$_3$): 40.62 (d, J=32.27, 1P), 36.72 (d, J=32.37, 1P). MS (ESI): 797.18 (62%, M), 762.12 (100%, [M−Cl]$^+$).

EXAMPLE 9: Dichloro[2-(diphenylphosphino)-N-(2-(methylthio)benzyl)ethanamine]-ruthenium(II) 9

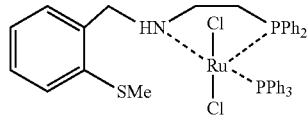

9

Under argon NaBH$_4$ (0.13 g, 3.47 mmol) is added to a solution of 2-(diphenylphosphino)-N-(2-(methylthio)benzylidene)ethanamine (0.42 g, 1.16 mmol) in ethanol (7 ml). After stirring for 20 h at 80° C. the reaction mixture is cooled to room temperature and DCM (10 ml) is added, followed by saturated aqueous NH$_4$Cl-solution. The phases were separated and the organic phase is washed twice with water and once with brine. The organic phase is dried over MgSO$_4$, filtered and concentrated under vacuo. Ligand 2-(diphenylphosphino)-N-(2-(methylthio)benzyl)ethanamine is obtained as a yellow liquid (0.36 g, 86%). Analytical data:

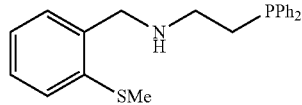

10 $^1$H-NMR (400 MHz, CDCl$_3$): 7.76 (m, 1H), 7.44 (m, 4H), 7.34 (m, 6H), 7.24 (m, 2H), 7.12 (m, 1H), 3.86 (s, 2H), 2.81 (m, 2H), 2.49 (s, 3H), 2.34 (m, 2H), 1.75 (bs, 1H). $^{13}$C-NMR (400 MHz, CDCl$_3$): 138.89, 138.25, 137.70, 133.13, 129.29, 128.95, 128.82, 128.05, 126.09, 125.31, 51.88, 46.43, 29.48, 16.17. $^{31}$P-NMR (500 MHz, CDCl$_3$): −20.60 (s, 1P). GC/MS: 350 (16%, [M−15]$^+$), 318 (40%), 200 (26%), 183 (32%), 166 (11%), 152 (19%), 137 (100%), 121 (33%), 108 (36%), 91 (25%), 77 (13%), 45 (28%).

Under argon dichlorotris(triphenylphosphine)ruthenium (II) (0.94 g, 0.99 mmol) is added to a solution of 2-(diphenylphosphino)-N-(2-(methylthio)benzyl)ethanamine (0.36 g, 0.99 mmol) in toluene (20 ml). After stirring for 19 h at 110° C. the reaction mixture is cooled to room temperature and evaporated under vacuo to a volume of 5 ml. To this suspension hexane (20 ml) is added. After stirring for 15 min the suspension is filtered and washed with hexane (4 ml) and diethyl ether (2×4 ml). The light-brown filter cake is dried under vacuo for 19 h and then suspended in diethyl ether (5 ml). After stirring for 15 min the suspension is filtered, washed with diethyl ether (3×1 ml) and the filter cake is dried under vacuo. Complex 9 is obtained as a light-brown solid (0.76 g, 96%). Analytical data:

$^1$H-NMR (400 MHz, CDCl$_3$): 7.80 (m, 6H), 7.69 (m, 1H), 7.47 (m, 3H), 7.31-7.01 (m, 17H), 6.88 (dt, J=2.02, 7.58, 1H), 7.18 (d, J=7.33, 1H), 5.48 (bs, 1H), 5.23 (d, J=12.63, 1H), 4.11 (m, 1H), 3.89 (m, 1H), 3.00 (m, 1H), 2.07 (m, 1H), 1.12 (m, 1H), 1.08 (s, 3H). $^{31}$P-NMR (500 MHz, CDCl$_3$): 49.83 (d, J=27.74, 1P), 37.96 (d, J=27.74, 1P). Anal. calcd. for C$_{40}$H$_{39}$Cl$_2$NP$_2$RuS: C, 60.07%; H, 4.92%; N, 1.75%. Found: C, 60.36%; H, 4.79%; N, 1.47%.

EXAMPLE 10: RuCl$_2$(2-(diphenylphosphino)-N-(2-(n-butoxy)ethyl)ethanamine)PPh$_3$ 10

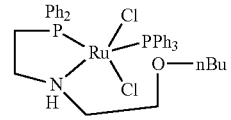

10

Under nitrogen, stirring and cooling NaH 60% in mineral oil (6.5 g, 162 mmol) is added portionwise to butanol (10 g, 135 mmol) in dry THF (70 ml) within 30 min. After 1 h at r.t. 2-bromo-1,1-dimethoxyethane (23.5 g, 135 mmol) in THF (20 ml) is added dropwise under slight cooling. The mixture is heated 44 h at reflux (67° C.) and (after complete conversion) cooled to r.t. and poured upon water (200 ml). Extraction with dichloromethane (2×200 ml), washing of the combined organic layers with water (200 ml), drying over MgSO$_4$, filtration and evaporation of the solvent gives 15.6 g (71%) of 1-(2,2-dimethoxyethoxy)butane as colorless liquid containing some (15%) n-butanol. Analytical data:

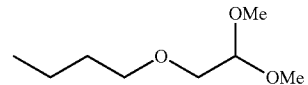

$^1$H-NMR (400 MHz, CDCl$_3$): 4.5 (t, 1H), 3.45-4.5 (2 m, 4H), 3.4 (s, 6H), 1.5-1.6 (m, 2 H), 1.4 (m, 2 H), 0.9 (t, 3 H) ppm. $^{13}$C-NMR (400 MHz, CDCl$_3$): 102.7 (d), 71.5 (t, OCH$_2$), 70.4 (t, OCH$_2$), 53.8 (q, OMe), 32.6 (t), 19.2 (t), 13.8 (q) ppm. GCMS: 131 (0.5%, [M−OMe]$^+$), 75 (100%, [n-Butyl-O—CH$_2$]$^+$), 57 (8%, [n-Butyl]$^+$), 45 (28%).

pTSA monohydrate (8.8 g, 46 mmol) dissolved in water (70 ml) is added to 1-(2,2-dimethoxyethoxy)-butane (5 g, 31 mmol) in DCM (50 ml). The mixture is stirred 46 h at 45° C. After phase separation and extraction of the water phase with DCM (50 ml), the combined organic layers are washed with conc. NaCO$_3$ (25 ml) and conc. NaCl (2×25 ml), dried over MgSO$_4$, filtered and evaporated at 500 mbar/40° C. The residue (3.25) is treated with butylhydroxytoluene (20 mg) and is bulb-to-bulb-distilled at 80-100° C./50 mbar to give 0.9 g (24%) of 2-butoxyacetaldehyde with 80% purity. The analytical data of this fraction was identical with the ones reported reported for this compound in H. C. Arndt, S. A. Caroll, *Synthesis*, 202, 1979 and the compound was used immediately in the next step. 2-Butoxyacetaldehyde (0.53 g, 4.56 mmol) in 1,2-dichloroethane (50 ml) is added to 2-(diphenylphosphino)-ethanamine (1.92 g, 8.0 mmol) under nitrogen and stirring. After addition of NaBH(OAc)$_3$ (1.5 g, 6.6 mmol) and 22 h stirring at r.t. the mixture is poured upon conc. NaHCO$_3$ (100 ml), the phases are separated and the water-phase extracted with 1,2-dichloroethane (50 ml). The organic layers are washed with conc. aqueous NaCl (50 ml). The aqueous layers are re-extracted with 1,2-dichloroethane (100 ml). The combined organic layers are dried over MgSO₄, filtered and evaporated to give 1.25 g of a yellowish oil which is taken up in ethyl acetate and purified by flash chromatography over silica gel using eluent ethyl acetate. Evaporation of the solvent gives SNP-ligand 2-butoxy-N-(2-(diphenylphosphino)ethyl)ethanamine (0.5 g, 37%). Analytical data:

$^1$H-NMR (CD$_2$Cl$_2$, 400 MHz): δ 7.4-7.45 (4 H, Ar), 7.3 (6 H, Ar), 3.5 (t, 2 H), 3.4 (t, 2 H), 2.7 2.8 (4 H), 2.3 (m, 2 H), 1.6-1.7 (br, 1 H, NH), 1.5-1.6 (m, 2 H), 1.3-1.4 (m, 2 H), 0.9 (t, 3 H) ppm. $^{13}$C-NMR (CD$_2$Cl$_2$, 400 MHz): δ 138.5 and 138.4 (s), 132.8 and 132.6 (d), 128.6 (d), 128.5 and 128.4 (d), 71.0 (t), 70.0 (t), 49.2 (t), 46.8 and 46.6 (t), 31.8 (t), 29.15 and 29.0 (t), 19.3 (t), 13.95 (q, Me) ppm. $^{31}$P-NMR (CD$_2$Cl$_2$, 200 MHz): −20.4 ppm. GSMS (EI) (m/z): 328 ([M−H]$^+$, 1%), 286 (1%), 272 (2%), 257 (9%), 255 (12%), 242 (33%), 229 (14%), 227 (32%), 201 (28%), 200 (71%), 199 (51%), 186 (60%), 185 (93%), 184 (11%), 183 (100%), 152 (12%), 130 (12%), 121 (33%), 109 (12%), 108 (43%), 107 (24%), 91 (18%), 74 (15%), 58 (88%), 57 (44%), 56 (52%), 41 (43%), 29 (28%).

ONP-ligand 2-(diphenylphosphino)-N-(2-(n-butoxy)ethyl)ethanamine (0.5 g, 1.5 mmol) and RuCl$_2$(PPh$_3$)$_3$ (1.05 g, 1.1 mmol) in dichloromethane (30 ml) are heated under reflux, stirring and nitrogen for 8 h. At room temperature hexane (150 ml) are added to the brown solution. The dark red precipitate is filtered, washed with hexane (3×20 ml) and dried under reduced pressure to give complex 10 (0.65 g, 56%) as a dark red powder. Analytical data of complex 10:

$^1$H-NMR (400 MHz, CD$_2$Cl$_2$): 7.4-7.5 (5 H), 7.0-7.3 (20 H), 5.1-5.2 (1 H), 4.0-4.1 (1 H), 3.9 (1 H), 3.2-3.6 (4 H), 2.6-2.9 (3 H), 1.55 (1H), 1.2-1.4 (3 H), 0.75-0.9 (2 H), 0.7 (3 H), 0.0 (3H). $^{31}$P-NMR (CD$_2$Cl$_2$, 400 MHz): δ 61.0 and 60.8 (d), 45.9 and 45.7 (d). MS (ESI(+), m/z, %): 728 ([M−Cl]$^+$, 100%, identical with calculated isotope cluster). IR (ATR): 3162 (w), 3059 (w), 3056 (w), 2946 (w), 2909 (w), 2866 (w), 1480 (w), 1432 (m), 1189 (w), 1091 (m), 1069 (w), 1019 (m), 921 (w), 833 (w), 806 (w), 739 (m), 691 (s), 655 (m), 618 (w). Anal. calcd. for C$_{38}$H$_{43}$Cl$_2$NP$_2$RuO: C, 59.77%; H, 5.68%; N, 1.83%. Found: C, 59.74%; H, 5.66%; N, 1.73%.

EXAMPLE 11: Catalytic hydrogenation of ethyl benzoate using RuCl$_2$(2-(diphenylphosphino)-N-(thiophen-2-ylmethyl)ethanamine)PPh$_3$ 1

Catalyst 1 (1.5 mg, 2 μmol) and ethyl benzoate (0.6 g, 4 mmol) are dissolved in toluene (10 ml) and placed in a 120 ml Premex autoclave under argon. After addition of sodium methylate (22 mg, 0.4 mmol) the argon atmosphere is replaced by hydrogen and the mixture is heated under stirring 16 h at 100° C. under 50 bar hydrogen. The pressure is released and the mixture treated at room temperature with 2% H$_3$PO$_4$ (30 ml). Extraction is carried out with t-butyl methyl ether (50 ml). GCMS-analysis reveals a quantitative conversion to benzyl alcohol with 99% purity.

EXAMPLE 12: Catalytic hydrogenation of Sclareolide with 0.05% RuCl$_2$(2-(diphenylphosphino)-N-(thiophen-2-ylmethyl)ethanamine)PPh$_3$ 1

Commercially available (+)-(3aR,5aS,9aS,9bR)-Sclareolide (CAS 564-20-5) was used as substrate.

Catalyst 1 (1.5 mg, 2 μmol) and Sclareolide (1 g, 4 mmol) are dissolved in toluene (10 ml) and placed in a 120 ml Premex autoclave under argon. After addition of sodium methylate (22 mg, 0.4 mmol) the argon atmosphere is replaced by hydrogen and the mixture is heated under stirring 16 h at 100° C. under 50 bar hydrogen. After work-up 1 g Sclareodiol (99.5%) is obtained with 100% purity according to GCMS and NMR analysis. The analytical data of (1R,2R,4aS,8aS)-Sclareodiol are consistent with the ones described for this compound (CAS 38419-75-9) in the literature, e.g. in J. H. George et al., Org. Lett. 14, 4710 (2012).

In the following table some variations of this transformation are described:

TABLE 1

| | | | General conditions as above (example 12). | | | | |
|---|---|---|---|---|---|---|---|
| run | Scale (a) | catalyst | Loading (b) | Sclareolide (c) | Sclareodiol | Ambrox | TON (d) |
| 1 | 1 g/10 ml | 1 | 0.05% | ./. | 100% | ./. | 2000 |
| 2 | 1 g/10 ml | 1 | 0.01% | 21% | 75% | 4% | 8000 |
| 3 | 26 g/63 ml | 2 | 0.01% | 8% | 88% | 5% | 9000 |
| 4 | 2 g/20 ml | 3 | 0.05% | ./. | 100% | ./. | 2000 |
| 5 | 1 g/10 ml | 3 | 50 ppm | 14% | 85% | 1% | 17000 |
| 6 | 26 g/63 ml | 3 | 50 ppm | 20% | 67% | 12% | 16000 |
| 7 | 1 g/10 ml | 4 | 0.01% | 2% | 98% | ./. | 9800 |
| 8 | 1 g/10 ml | 4 | 25 ppm | 3% | 96% | 1% | 39000 |
| 9 | 1 g/10 ml | 4 | 10 ppm | 20% | 77% | 3% | 80000 |

(a) Substrate/solvent scale.
(b) Catalyst loading/substrate in mol % or mol-ppm.
(c) Substrate Sclareolide (CAS 564-20-5).
(d) Turnover numbers as deduced from the conversion detected in the crude product.

EXAMPLE 13: Catalytic Hydrogenation of Sclareolide with Ru(II)-Catalyst and Base KOMe in THF Catalyst 3 (1.9 mg, 2.6 μmol) dissolved under ultrasound 5-10 min in THF (5 ml) is added under argon to Sclareolide (26 g, 104 mmol) in THF (58 ml) in a Premex autoclave. After addition of KOMe (0.72 g, 10.4 mmol) the argon atmosphere is replaced by hydrogen and the mixture is heated under stirring 22 h at 100° C. under 50 bar hydrogen. After cooling to r.t. pressure is released and the reaction mixture poured onto aqueous 2% H$_3$PO$_4$ under stirring. Extraction with tert-butylmethylether (2×50 ml), washing of the combined organic layers with water (50 ml), drying over MgSO$_4$, filtration and evaporation of the solvents gives 26.4 g of a white solid, consisting of Sclareodiol (94%), Ambrox (2%) and Sclareolide (3%) according to GC and NMR.

In the following table some variations of this transformation are described:

TABLE 2

General conditions as above (example 13).

| run | Scale (a) | catalyst | loading (b) | Sclareolide (c) | Sclareodiol | Ambrox | TON (d) |
|---|---|---|---|---|---|---|---|
| 1 | 26 g/63 ml | 3 | 50 ppm | ./. | 98% | 1 | 19800 |
| 2 | 26 g/63 ml | 3 | 25 ppm | 3% | 94% | 3% | 39000 |
| 3[e] | 26 g/63 ml | 4 | 25 ppm | 1.5% | 97% | 1.5% | 39400 |
| 4 | 250 g/630 ml | 4 | 25 ppm | ./. | 95% | 5% | 40000 |
| 5 | 26 g/63 ml | 5 | 0.01% | ./. | 99% | 1% | 10000 |
| 6 | 26 g/63 ml | 5 | 25 ppm | 4% | 92% | 3% | 38000 |
| 7 | 26 g/63 ml | 10 | 0.1% | 66% | 29% | 4% | 290 |
| 8 | 26 g/63 ml | 10 | 0.01% | 96% | 2% | ./. | 200 |

(a) Substrate/solvent scale.
(b) Catalyst loading/substrate in mol %.
(c) Substrate Sclareolide (CAS 564-20-5).
(d) Turnover numbers as deduced from the conversion detected in the crude product.
[e] 4 mol % KOMe instead of 10 mol %.

EXAMPLE 14: Catalytic Hydrogenation of Sclareolide with Ru(II)-Catalyst 4 and Bases NaH or KH Catalyst 4 (2 mg, 2.6 μmol) dissolved under ultrasound 5-10 min in toluene (20 ml) is added under argon to Sclareolide (26 g, 104 mmol) in toluene (43 ml) in a Premex autoclave. After addition of potassium hydride 35% in paraffine oil (1.2 g, 10.4 mmol) the argon atmosphere is replaced by hydrogen and the mixture is heated under stirring 7 h at 105° C. under 50 bar hydrogen. After cooling to r.t. pressure is released and the reaction mixture poured onto aqueous 2% $H_3PO_4$ (30 ml) under stirring. Extraction with tert-butylmethylether and ethyl acetate, drying over $MgSO_4$, filtration and evaporation of the solvents gives 27.2 g of a white solid, consisting of Sclareodiol (94%), Ambrox (5%) and Sclareolide (1%) according to GC.

The same procedure using sodium hydride 60% in paraffine oil and solvent THF under otherwise identical conditions and ratios gave 26.5 g of a white solid, consisting of Sclareodiol (95%), Ambrox (3%) and Sclareolide (2%) according to GC.

EXAMPLE 15: Catalytic Hydrogenation α/β-Unsaturated Ester 11

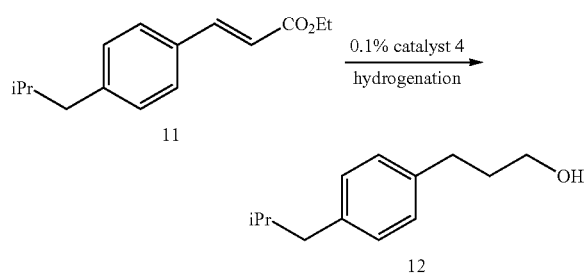

Commercially available (E)-ethyl 3-(4-isobutylphenyl) acrylate 11 (3 g, 12.4 mmol), catalyst 4 (9.7 mg, 12 μmol) and KOMe (92 mg, 1.24 mmol) in THF (30 ml) are hydrogenated 16 h in a Parr-autoclave at 105° C. under hydrogen (50 bar) and stirring. After cooling to r.t. pressure is released and the reaction mixture poured onto aqueous 2% $H_3PO_4$ (10 ml) under stirring. After extraction with tert-butylmethylether(20 ml) the organic layers are washed with brine (20 ml). Drying over $MgSO_4$, filtration and evaporation of the solvents and bulb-to-bulb distillation at 120-140° C./0.05 mbar gives 2.6 g (91%) of 3-(4-isobutylphenyl) propan-1-ol 12 as a colorless oil and a GC-purity of 97-100%. Analytical data:

15 $^1$H-NMR (400 MHz, CDCl$_3$): 7.0-7.1 (4 H), 3.6 (t, 2 H), 2.65 (t, 2 H), 2.4 (d, 2 H), 1.85-1.9 (3 H), 1.7 (br, OH, 1 H), 0.9 (d, 6 H) ppm. $^{13}$C-NMR (400 MHz, CDCl$_3$): 139.2 (s), 139.0 (s), 129.2 (d), 128.1 (d), 62.4 (t), 45.1 (t), 34.3 (t), 31.7 (t), 30.3 (d), 22.4 (q) ppm. GCMS: 192 (27%, [M]$^+$), 174 (4%, [M–H$_2$O]$^+$), 149 (83%), 132 (14%), 131 (100%), 117 (24%), 116 (12%), 115 (15%), 105 (26%), 104 (12%), 91 (32%). IR (film): 3326 (br), 3009 (w), 2951 (s), 2925 (m), 2867 (m), 1512 (m), 1465 (m), 1418 (m), 1383 (m), 1366 (m), 1166 (w), 1116 (w), 1058 (m), 1039 (s), 1021 (w), 915 (w), 846 (m), 810 (w), 791 (m), 695 (s).

The same reaction with 0.01% catalyst 4 (1 mg, 1.24 μmol) under otherwise identical conditions gave saturated ester 15 (2.91 g) as a yellow oil containing 82% saturated ester and 18% 3-(4-isobutylphenyl)propan-1-ol 12. Analytical data of 15:

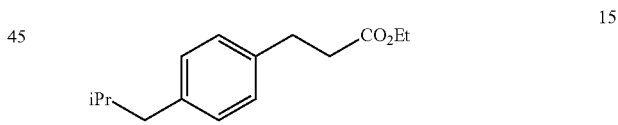

$^1$H-NMR (400 MHz, CDCl$_3$): 7.0-7.1 (4 H), 4.2 (q, 1 H), 2.9 (t, 2 H), 2.6 (t, 2 H), 2.4 (d, 2 H), 1.8-1.9 (1 H), 1.2 (t, 3 H), 0.9 (d, 6 H) ppm. $^{13}$C-NMR (400 MHz, CDCl$_3$): 173.1 (s, C=O), 139.6 (s), 137.8 (s), 129.2 (d), 128.0 (d), 60.4 (t), 45.0 (t), 36.1 (t), 30.25 (t), 30.24 (d), 22.4 (2 C, q), 14.2 (q) ppm. GCMS: 234 (10%, [M]$^+$), 191 (26%), 160 (33%), 147 (11%), 118 (18%), 117 (100%), 104 (14%), 91 (12%).

EXAMPLE 16: Catalytic Hydrogenation of Unsaturated Ester 13

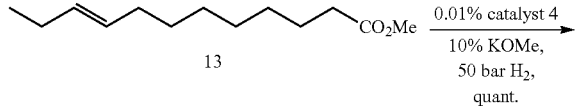

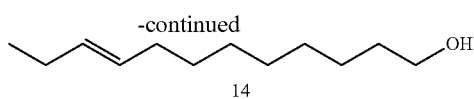

14

For the synthesis of methyl dodec-9-enoate 13 see for example K. Takai, *Organic Reactions* 64, pages 253, 488 (2004).

A mixture of methyl dodec-9-enoate 13 E/Z 84:16 (30 g, 141 mmol), KOMe (1.05 g, 14.11 mmol) and catalyst 4 (11 mg, 14 mol) is hydrogenated (50 bar) at 80° C. and under stirring for 21 h. After cooling to r.t. pressure is released and the reaction mixture poured onto aqueous 2% $H_3PO_4$ (30 ml) under stirring. After extraction with tert-butylmethylether the organic layers are washed with brine (20 ml). Drying over $MgSO_4$, filtration and evaporation of the solvents gives 27 g of a yellowish oil which is purified by distillation at 62-72° C./0.05 mbar giving 21.5 g (83%, corr) of dodec-9-en-1-ol 14 with 93-98% purity and an E/Z ratio of 85/15. The analytical data of the isomers are identical with the ones from the literature (H. J. Bestmann et al., *Chem. Ber.* 113, 1115, 1980, and references therein).

EXAMPLE 17: slightly modified procedure for the synthesis of catalyst $RuCl_2$(2-(diphenylphosphino)-N-(2-(methylthio)ethyl)ethanamine)$PPh_3$ 3 with correct elemental analysis

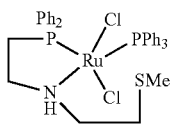

3

Methylthioethanal was prepared as described in Synthesis 7, 659 (1987) from (2,2-dimethoxyethyl)(methyl)sulfane.

Under nitrogen and stirring NaBH(OAc)$_3$ (2.85 g, 12.75 mmol) is added to 2-(diphenylphosphino)-ethanamine (1.92 g, 8.0 mmol) and methylthioethanal (0.82 g, 8.75 mmol) in 1,2-dichloroethane (50 ml). After 22 h stirring at room temperature the mixture is poured upon conc. NaHCO$_3$ (50 ml) and extracted with 1,2-dichloroethane (50 ml). The organic layers are washed with conc. aqueous NaCl (50 ml). The aqueous combined aqueous layers are re-extracted with 1,2-dichloroethane. The combined organic layers are dried over MgSO$_4$, filtered and evaporated to give 2.83 g of a yellowish oil which is taken up in ethyl acetate and purified by flash chromatography over silica gel using eluent ethyl acetate. Evaporation of the solvent gives SNP-ligand 2-(diphenylphosphino)-N-(2-(methylthio)ethyl)-ethanamine (1.2 g, 45%). Analytical data:

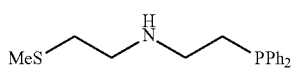

$^1$H-NMR (CD$_2$Cl$_2$, 400 MHz): δ 7.4-7.45 (4 H, Ar), 7.3-7.35 (6 H, Ar), 2.7-2.8 (4 H), 2.5 2.6 (m, 2 H), 2.2-2.3 (m, 2 H), 2.05 (3 H), 1.7 (br, 1 H, NH) ppm. $^{13}$C-NMR (CD$_2$Cl$_2$, 400 MHz): δ 138.8 (s), 132.7 (d), 128.4-128.8 (2 d), 47.8 (t), 46.3 and 46.1 (t), 34.4 (t), 29.1 and 28.9 (t), 15.1 (q, SMe) ppm. $^{31}$P-NMR (CD$_2$Cl$_2$, 200 MHz): −20.7 ppm. GSMS (EI) (%) (m/z): 288 ([M−CH$_3$]$^+$, 8%), 256 ([M+O−

MeSH]$^+$, 80%), 242 (8%), 199 (19%), 185 (100%), 183 (89%), 152 (11%), 121 (27%), 108 (20%), 107 (21%), 91 (11%), 75 (43%), 61 (14%).

SNP-Ligand 2-(diphenylphosphino)-N-(2-(methylthio) ethyl)ethanamine (0.5 g, 1.65 mmol) and RuCl$_2$(PPh$_3$)$_3$ (1.15 g, 1.15 mmol) in dichloromethane (30 ml) are heated under reflux, stirring and nitrogen for 22 h. At room temperature hexane (150 ml) is slowly added to the organge suspension under stirring. The precipitate is filtered, washed with hexane (20 ml) and dried under high vacuum to give complex 3 (0.79 g, 93%) as an orange solid. Analytical data:

$^{31}$P-NMR (CD$_2$Cl$_2$, 400 MHz): δ 46.1 and 44.7 (2 d, 30.5 Hz, major isomer), 46.6 and 44.4 (2 d, 32.5 Hz, minor isomer). MS (EI in MeOH, HCO$_2$H, %, m/z): 742 (100%), 702 ([M−Cl]$^+$, 82%). IR (ATR): 3162 (w), 3047 (w), 2914 (w), 2857 (w), 1480 (w), 1454 (w), 1431 (m), 1299 (w), 1184 (w), 1086 (m), 1012 (w), 979 (w), 958 (w), 864 (w), 801 (w), 740 (m), 691 (s), 658 (m), 619 (w). Anal. calcd. for C$_{35}$H$_{37}$Cl$_2$NP$_2$RuS: C, 56.99%; H, 5.06%; N, 1.9%. Found: C, 56.81%; H, 5.20%; N, 1.98%.

EXAMPLE 18: slightly modified procedure for the synthesis of catalyst RuCl$_2$(2-(diphenylphosphino)-N-(2-(n-butylthio)ethyl)ethanamine)PPh$_3$ 4 with correct elemental analysis

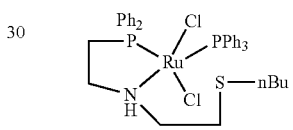

4

For the synthesis of n-butylthioethanal see N. A. Keiko et al. *Arkivoc* 127-138 (2011).

Under nitrogen and stirring NaBH(OAc)$_3$ (3 g, 13.3 mmol) is added to 2-(diphenylphosphino)-ethanamine (2 g, 8.3 mmol) and n-butyllthioethanal (1.2 g, 9.1 mmol) in 1,2-dichloroethane (50 ml). After 22 h stirring at room temperature the mixture is poured upon conc. NaHCO$_3$ and is extracted with DCE. The organic layers are washed with conc. aqueous NaCl. The aqueous phase is re-extracted with DCE. The combined organic layers are dried over MgSO$_4$, filtered and evaporated to give 3.15 g of a yellowish oil which is taken up in ethyl acetate and purified by flash chromatography over silica gel using eluent ethyl acetate. In a first fraction by product 2-(butylthio)-N-(2-(butylthio) ethyl)-N-(2-(diphenylphosphino)ethyl)ethanamine (0.72 g, 19%, after solvent evaporation) is separated. Analytical data:

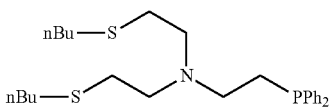

$^1$H-NMR (CD$_2$Cl$_2$, 400 MHz): δ 7.4 (4 H, Ar), 7.3 (6 H, Ar), 2.7-2.6 (6 H), 2.45-2.55 (8 H), 2.2 (2 H), 1.5-1.6 (4 H), 1.35-1.45 (4 H), 0.9 (t, 6 H) ppm. $^{13}$C-NMR (CD$_2$Cl$_2$, 400 MHz): δ 138.8 (s), 132.65 (d), 130.55 (d), 128.55 (d), 53.9 (t), 50.2 (t), 32.0 (t), 29.8 (t), 25.7 (t), 22.0 (t), 13.5 (q, Me) ppm. $^{31}$P-NMR (CD$_2$Cl$_2$, 200 MHz): −20.0 ppm. MS (EI) (m/z): 404 ([M−C4H9]$^+$), 373 (23%), 372 (90%), 358 (100%), 288 (6%), 256 (8%), 186 (9%), 185 (61%), 183 (25%), 117 (55%), 61 (16%). 57 (11%). IR (film): 3052 (w), 2954 (m), 2926 (m), 2870 (m), 1738 (w), 1586 (w), 1480 (w), 1457 (m), 1434 (m), 1377 (w), 1294 (w), 1192 (m), 1095 (m), 1069 (w), 1026 (w), 998 (w), 914 (w), 737 (m), 695 (s).

Evaporation of the solvent from the second fraction gives SNP-ligand 2-(diphenylphosphino)-N-(2-(methylthio)ethyl) ethanamine (0.77 g, 27%). Analytical data:

$^1$H-NMR (CD$_2$Cl$_2$, 400 MHz): δ 7.4-7.45 (4 H, Ar), 7.3-7.35 (6 H, Ar), 2.7 (4 H), 2.6 (m, 2 H), 2.5 (2 H), 2.3 (m, 2 H), 1.6 (br, 1 H, NH), 1.5 (m, 2 H), 1.4 (m, 2 H), 0.9 (t, 3 H) ppm. $^{13}$C-NMR (CD$_2$Cl$_2$, 400 MHz): δ 138.85 (s), 132.65 (d), 130.55 (d), 128.45 (d), 48.5 (t), 46.2 (t), 32.3 (t), 31.9 (t), 31.6 (t), 28.95 (t), 22.0 (t), 13.5 (q, Me) ppm. $^{31}$P-NMR (CD$_2$Cl$_2$, 200 MHz): −20.7 ppm. MS (EI) (m/z): 346 ([M+H]$^+$, 289 (10%), 288 (55%), 257 (18%), 256 ([M+O−BuSH]$^+$, 100%), 242 (20%), 199 (13%), 186 (18%), 185 (87%), 183 (31%), 69 (20%). IR (film): 3051 (w), 2926 (m), 2871 (w), 1953 (w), 1886 (w), 1812 (w), 1737 (w), 1671 (w), 1585 (w), 1479 (w), 1456 (m), 1433 (m), 1376 (w), 1331 (w), 1272 (w), 1240 (w), 1184 (w), 1117 (m), 1068 (w), 998 (w), 737 (m), 694 (s).

SNP-ligand 2-(diphenylphosphino)-N-(2-(n-butylthio) ethyl)ethanamine (0.25 g, 0.7 mmol) and RuCl$_2$(PPh$_3$)$_3$ (0.5 g, 0.5 mmol) in dichloromethane (15 ml) are heated under reflux, stirring and nitrogen for 24 h. At room temperature hexane (100 ml) are added. The precipitate is filtered, washed with hexane (3×20 ml) and dried under reduced pressure to give complex 4 (0.35 g, 88%) as an orange powder. Analytical data:

$^1$H-NMR (400 MHz, CD$_2$Cl$_2$): 6.9-7.4 (25 H), 4.5 and 4.7 (1 H), 2.3-3.7 (9 H), 1.55 (2H), 1.0-1.5 (4 H), 0.8 (t, 3H). $^{31}$P-NMR (CD$_2$Cl$_2$, 400 MHz): δ 45.6 and 45.9 (2 d), 44.7 and 44.8 (2 d). MS (ESI(+) in MeOH, HCO$_2$H, %, m/z): 754 ([M−Cl−HCl+HCO$_2$H]$^+$, 100%, identical with calculated isotope cluster), 744 ([M−Cl]$^+$, 100%). IR (ATR): 3162 (w), 3059 (w), 2947 (w), 2859 (w), 1585 (w), 1480 (w), 1454 (w), 1432 (m), 1303 (w), 1267 (w), 1187 (w), 1156 (w), 1138 (w), 1088 (m), 1067 (w), 1027 (w), 1006 (w), 983 (m), 914 (w), 865 (w), 799 (w), 751 (w), 740 (m), 737 (m), 691 (s), 657 (m), 619 (m). Anal. calcd. for C$_{38}$H$_{43}$Cl$_2$NP$_2$RuS: C, 58.53%; H, 5.56%; N, 1.80%. Found: C, 58.24%; H, 5.54%; N, 1.71%.

The invention claimed is:

1. A transition metal complex according to the formula:

MX$_2$[SNP]Y wherein M is a group VIII transition metal and SNP represents a tridentate or bisdentate ligand containing a nitrogen, sulphur and phosphorus atom, of which at least the N- and P- and optionally also the S-atom coordinates with the transition metal, each X is independently selected from a halide, hydroxyl, alkoxy, acyloxy and amido; and each Y is independently selected from a monodentate phosphine, a carbon monoxide (CO) ligand, a nitrosyl group and a RCN group, wherein R is alkyl or aryl, wherein the tridentate or bisdentate ligand is represented by the formula

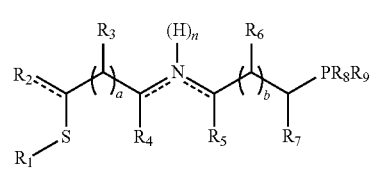

wherein

R$_1$ and R$_2$ are independently selected from H, or C$_1$ to C$_{20}$ alkyl and aryl, or R$_1$ and R$_2$ are connected such that together with the sulphur and carbon atoms to which they are attached, they form a heteroaliphatic or heteroaromatic ring;

R$_3$ through R$_7$ are independently selected from H; a C$_1$ to C$_{20}$ linear or branched alkyl group or alkenyl group; a C$_3$ to C$_8$ cyclic alkyl group; and a C$_5$ to C$_{10}$ aryl group; or R$_2$ and R$_3$; R$_3$ and R$_4$; or R$_2$ and R$_4$, together with the carbon atoms to which they are attached form a 5- or 6-membered aliphatic ring, which is optionally unsaturated; and/or R$_5$ and R$_6$; R$_5$ and R$_7$; or R$_6$ and R$_7$, together with the carbon atoms to which they are attached form a 5- or 6- membered aliphatic ring, which is optionally unsaturated;

R$_8$ and R$_9$ independently are selected from H; a C$_1$ to C$_{20}$ linear or branched alkyl group or alkenyl group; a C$_3$ to C$_8$ cyclic alkyl group; and a C$_5$ to C$_{10}$ aryl or heteroaryl group;

a and b are independently 0, 1 or 2;

n is 0 or 1; and

====== represents a single or a double bond, provided that when R$_2$ is H or C$_4$ to C$_{20}$ alkyl ====== represents a single bond; and when n is 1 each N ====== represents a carbon-nitrogen single bond; whereas when n is 0, one N ====== is a carbon-nitrogen single bond and the other N ====== is a carbon-nitrogen double bond.

2. A complex according to claim 1 wherein the nitrogen atom on the tridentate or bisdentate ligand forms part of an amine group or an imine group; the sulphur atom forms part of an aliphatic group or forms part of an aromatic ring; and the phosphorus atom forms part of a phosphine group.

3. A complex according to claim 1, wherein the nitrogen atom-containing group is flanked on one side by the phosphorus atom-containing group, and on the other side by the sulphur atom-containing group.

4. A complex according to claim 1, wherein the tridentate or bisdentate ligand is represented by the formula

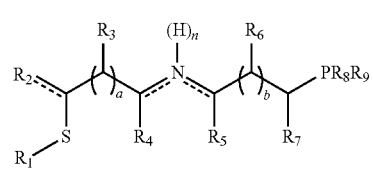

wherein

R$_1$ and R$_2$ are independently selected from H, or C$_1$ to C$_{20}$ alkyl or aryl, or R$_1$ and R$_2$ are connected such that together with the sulphur and carbon atoms to which they are attached, they form a heteroaliphatic or heteroaromatic ring;

R$_3$ through R$_7$ are independently selected from H; a C$_1$ to C$_{20}$ linear or branched alkyl group or alkenyl group; a $C_3$ to $C_8$ cyclic alkyl group; and a $C_5$ to $C_{10}$ aryl group; or $R_2$ and $R_3$; $R_3$ and $R_4$; or $R_2$ and R4, together with the carbon atoms to which they are attached form a 5- or 6-membered aliphatic ring, which is optionally unsaturated; and/or $R_5$ and $R_6$; $R_5$ and $R_7$; or $R_6$ and $R_7$, together with the carbon atoms to which they are attached form a 5- or 6-membered aliphatic ring, which is optionally unsaturated;

$R_8$ and $R_9$ independently are selected from H; a $C_1$ to $C_{20}$ linear or branched alkyl group or alkenyl group; a $C_3$ to $C_8$ cyclic alkyl group; and a $C_5$ to $C_{10}$ aryl or heteroaryl group;

a and b are independently 0, 1 or 2;

n is 0 or 1; and

≡≡≡≡≡ represents a single or a double bond, provided that when $R_2$ is H or $C_4$ to $C_{20}$ alkyl ≡≡≡≡≡ represents a single bond; and when n is 1 each N ≡≡≡≡≡ represents a carbon-nitrogen single bond; whereas when n is 0, one N ≡≡≡≡≡ is a carbon-nitrogen single bond and the other N ≡≡≡≡≡ is a carbon-nitrogen double bond.

5. A complex according to claim 1, wherein the tridentate or bisdentate ligand is represented by the formula selected from the group consisting of

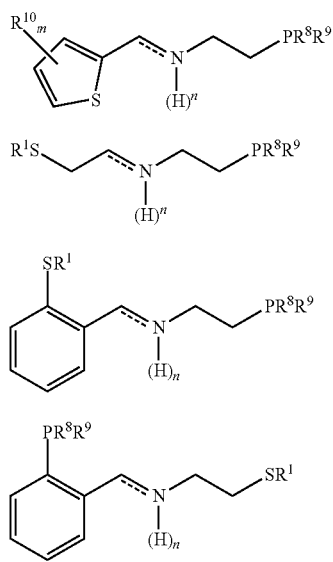

wherein $R^{10}$ is a moiety selected from $C_{1-10}$ alkyl, aryl, heteroaryl, alkenyl, nitrile and halide, and m is 0, 1, 2 or 3.

6. A complex according to claim 1, wherein the metal M is ruthenium or osmium.

7. A tridentate or bisdentate ligand L presented by the formula

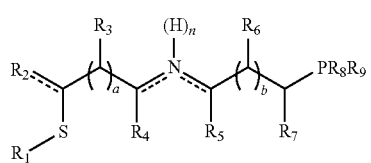

wherein $R_1$ and $R_2$ are independently selected from H, and $C_1$ to $C_{20}$ alkyl or aryl, or $R_1$ and $R_2$ are connected such that together with the sulphur and carbon atoms to which they are attached, they form a heteroaromatic or heteroaliphatic ring, and wherein said heteroaromatic ring is not a 5-membered heterocycle containing both S and N atoms;

$R_3$ through $R_7$ are independently selected from H; a $C_1$ to $C_{20}$ linear or branched alkyl group or alkenyl group; a $C_3$ to $C_8$ cyclic alkyl group; and a $C_5$ to $C_{10}$ aryl group; or $R_2$ and $R_3$; $R_3$ and $R_4$; or $R_2$ and $R_4$, together with the carbon atoms to which they are attached form a 5- or 6-membered aliphatic ring, which is optionally unsaturated; and/or $R_5$ and $R_6$; $R_5$ and $R_7$; or $R_6$ and $R_7$, together with the carbon atoms to which they are attached form a 5- or 6-membered aliphatic ring, which is optionally unsaturated; $R_8$ and $R_9$ independently are selected from H; a $C_1$ to $C_{20}$ linear or branched alkyl group or alkenyl group; a $C_3$ to $C_8$ cyclic alkyl group; and a $C_5$ to $C_{10}$ aryl or heteroaryl group;

a and b are independently 0, 1 or 2;

n is 0 or 1; and

≡≡≡≡≡ represents a single or a double bond, provided that when $R_2$ is H or $C_4$ to $C_{20}$ alkyl, ≡≡≡≡≡ represents a single bond; and when n is 1 each N ≡≡≡≡≡ represents a carbon-nitrogen single bond; whereas when n is 0, one N ≡≡≡≡≡ is a carbon-nitrogen single bond and the other N ≡≡≡≡≡ is a carbon-nitrogen double bond; with the proviso that the ligand L is not

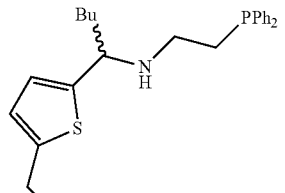

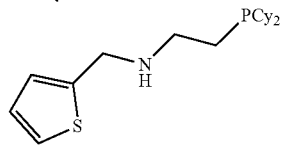

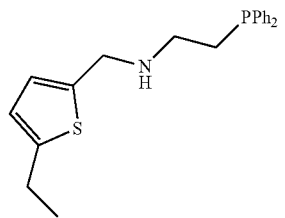

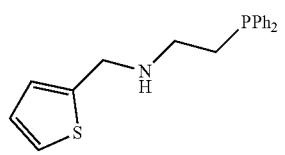

wherein the tridentate or bisdentate ligand is represented by the formula selected from the group consisting of
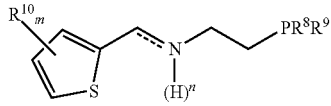 L1
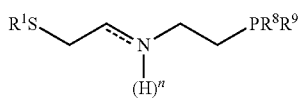 L2
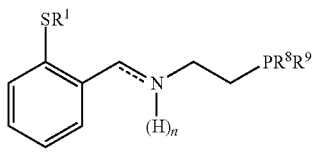 L3
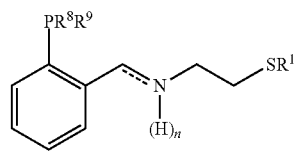 L4
wherein
R$^{10}$ is a moiety selected from C$_{1-10}$ alkyl, aryl, heteroaryl, alkenyl, nitrile and halide, and
m is 0,1,2 or 3.
8. A tridentate or bisdentate ligand according to claim 7 represented by the formula selected from the group consisting of
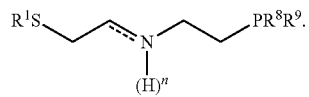 L2
* * * * *